(12) United States Patent
Itoi

(10) Patent No.: US 9,318,711 B2
(45) Date of Patent: Apr. 19, 2016

(54) ORGANIC ELECTROLUMINESCENCE MATERIALS COMPRISING SUBSTITUTED CARBAZOLES AND ORGANIC ELECTROLUMINESCENCE DEVICES HAVING THE SAME

(71) Applicant: SAMSUNG DISPLAY CO., LTD., Yongin, Gyeonggi-Do (KR)

(72) Inventor: Hiroaki Itoi, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 0 days.

(21) Appl. No.: 14/084,907

(22) Filed: Nov. 20, 2013

(65) Prior Publication Data

US 2014/0142301 A1     May 22, 2014

(30) Foreign Application Priority Data

Nov. 20, 2012     (JP) ................................. 2012-254159

(51) Int. Cl.
*C07D 209/86* (2006.01)
*H01L 51/00* (2006.01)
*C07D 471/04* (2006.01)
*H01L 51/50* (2006.01)

(52) U.S. Cl.
CPC .......... *H01L 51/0072* (2013.01); *C07D 471/04* (2013.01); *H01L 51/0081* (2013.01); *H01L 51/0085* (2013.01); *H01L 51/5016* (2013.01)

(58) Field of Classification Search
CPC .................................................... C07D 209/86
USPC ........................................................ 548/440
See application file for complete search history.

(56) References Cited

FOREIGN PATENT DOCUMENTS

| JP | 2001-160488 | 6/2001 |
| JP | 2006-100537 | 4/2006 |
| JP | 2009-088538 | 4/2009 |
| JP | 2010-135467 | 6/2010 |
| WO | WO-2004/053019 A1 | 6/2004 |
| WO | WO-2006/013739 A1 | 2/2006 |
| WO | WO-2006/112265 A1 | 10/2006 |
| WO | WO-2008/146838 A1 | 12/2008 |
| WO | WO-2009/060780 A1 | 5/2009 |
| WO | WO-2011/132684 A1 | 10/2011 |
| WO | WO-2012/011756 A1 | 1/2012 |
| WO | WO-2012/090967 A1 | 7/2012 |
| WO | WO 2013/105206 * | 7/2013 |

* cited by examiner

*Primary Examiner* — Douglas M Willis
(74) *Attorney, Agent, or Firm* — Lee & Morse, P.C.

(57) ABSTRACT

The organic EL material is represented by Formula (1):

where $X_1$ to $X_4$ are each independently a nitrogen (N) atom or a carbon atom that is monovalently bonded to $R_1$($C$—$R_1$), $R_1$ is a hydrogen atom, a halogen atom, an aryl group having 6 to 18 carbon atoms, a hetero aryl group having 6 to 18 carbon atoms, or an alkyl group having 1-12 carbon atoms, $R_2$ to $R_{10}$ are each independently hydrogen, an aryl group having 6 to 30 carbon atoms, or hetero aryl group having 6 to 30 carbon atoms, and at least one of $X_1$ to $X_4$ is a nitrogen atom.

7 Claims, 1 Drawing Sheet

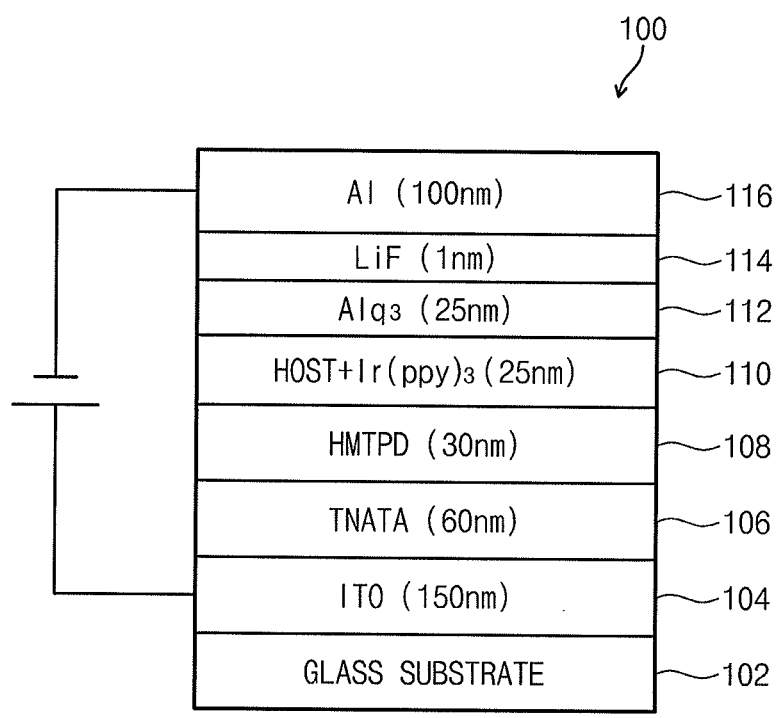

ORGANIC ELECTROLUMINESCENCE MATERIALS COMPRISING SUBSTITUTED CARBAZOLES AND ORGANIC ELECTROLUMINESCENCE DEVICES HAVING THE SAME

CROSS-REFERENCE TO RELATED APPLICATION

Japanese Patent Application No. 2012-254159, filed on Nov. 20, 2012, in the Japanese Intellectual Property Office, and entitled: "Organic Electroluminescence Material Comprising Azacarbazole Derivative and Organic Electroluminescence Device Having the Same," is incorporated by reference herein in its entirety.

BACKGROUND

1. Field

Embodiments relate to an organic EL material and an organic EL device including the same.

2. Description of the Related Art

In recent years, organic electroluminescence (EL) displays, which are one type of image displays, have been actively developed. Unlike a liquid crystal display and the like, the organic EL display is a so-called self-luminescent display in which holes and electrons injected from an anode and a cathode are recombined in a light-emitting layer to thus emit a light from a light-emitting material including an organic compound of the light-emitting layer, thereby displaying an image.

An example of a general light-emitting device may include an organic EL device that includes an anode, a hole transport layer disposed on the anode, a light-emitting layer disposed on the hole transport layer, an electron transport layer disposed on the light-emitting layer, and a cathode disposed on the electron transport layer. Holes injected from the anode may be transported into the light-emitting layer via the hole transport layer, and electrons may be injected from the cathode, and then transported into the light-emitting layer via the electron transport layer. The holes and the electrons injected into the light-emitting layer recombine to generate excitons within the light-emitting layer. The organic EL device emits a light by using light generated by radiation and non-activation of the excitons. The organic EL device may be changed in various forms from the above-described configuration.

SUMMARY

Embodiments are directed to an organic EL material represented by Formula 1, below:

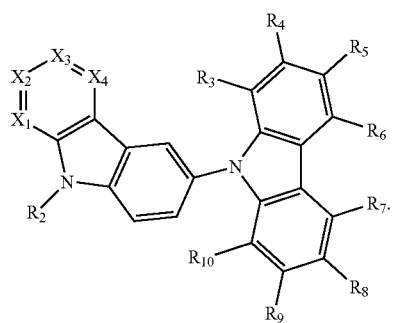

Formula 1

In Formula 1, $X_1$ to $X_4$ are each independently a nitrogen (N) atom or a carbon atom that is monovalently bonded to a substituent $R_1$, where $R_1$ is a hydrogen atom, a halogen atom, an aryl group having 6 to 18 carbon atoms, a heteroaryl group having 6 to 18 carbon atoms, or an alkyl group having 1-12 carbon atoms. $R_2$ to $R_{10}$ are each independently hydrogen, an aryl group having 6 to 30 carbon atoms, or a heteroaryl group having 6 to 30 carbon atoms. At least one of $X_1$ to $X_4$ is a nitrogen atom.

One or more of $R_2$ to $R_{10}$ may independently be one of the monovalent groups represented by Groups (2) to (11), below:

Groups (2) to (11)

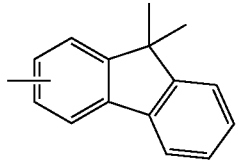

(2)

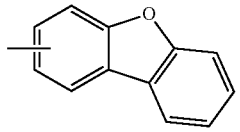

(3)

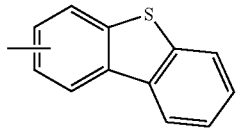

(4)

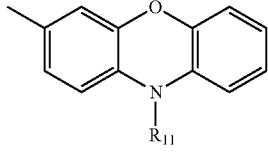

(5)

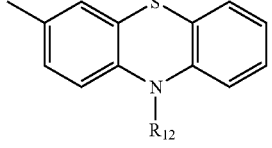

(6)

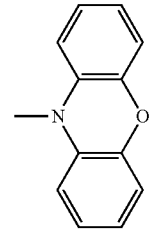

(7)

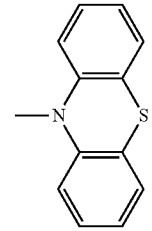

(8)

Groups (2) to (11)

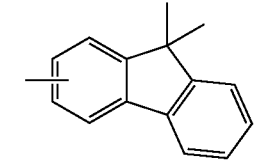 (2)

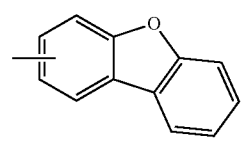 (3)

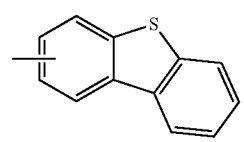 (4)

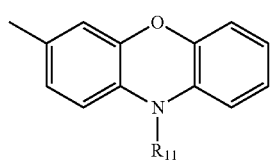 (5)

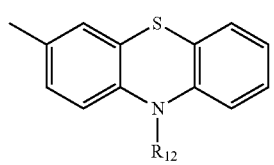 (6)

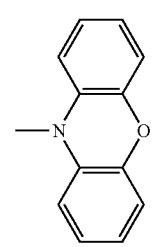 (7)

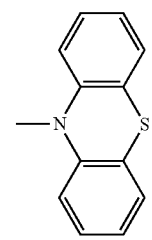 (8)

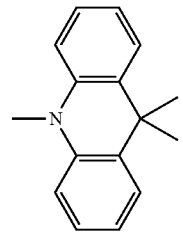 (9)

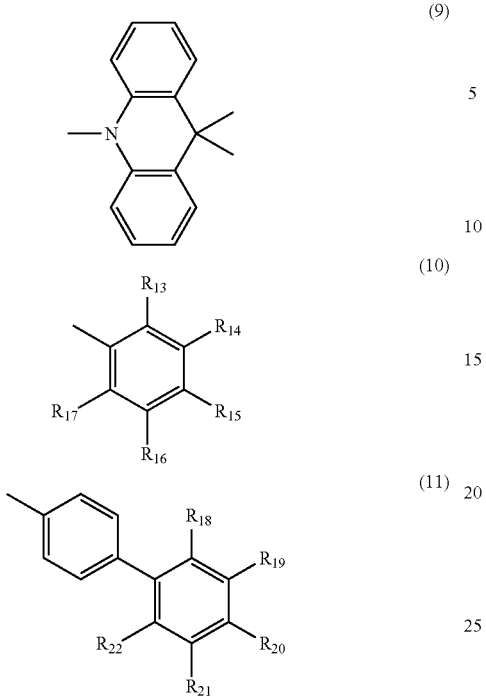

(9)

(10)

(11)

$R_{11}$ to $R_{22}$ may each independently be a hydrogen atom, a halogen atom, an aryl group having 6 to 18 carbon atoms, a hetero aryl group having 6 to 18 carbon atoms, or an alkyl group having 1 to 12 carbon atoms.

$R_1$ may be a phenyl group, a methyl group, or a cyclohexyl group.

Embodiments are also directed to an organic EL device including an organic EL material represented by Formula 1, below:

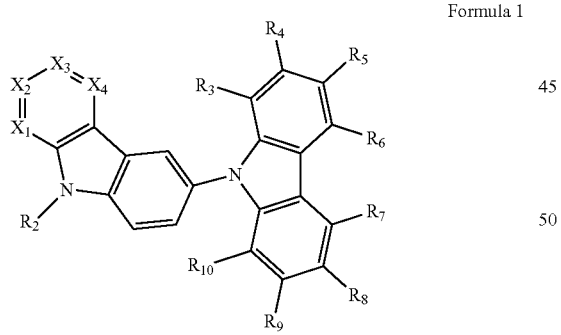

Formula 1

In Formula 1, $X_1$ to $X_4$ are each a nitrogen (N) atom or a carbon atom that is monovalently bonded to a substituent $R_1$ (C—$R_1$), where $R_1$ is a hydrogen atom, a halogen atom, an aryl group having 6 to 18 carbon atoms, a hetero aryl group having 6 to 18 carbon atoms, or an alkyl group having 1-12 carbon atoms. $R_2$ to $R_{10}$ are each independently hydrogen, an aryl group having 6 to 30 carbon atoms, or a hetero aryl group having 6 to 30 carbon atoms. At least one of $X_1$ to $X_4$ is a nitrogen atom.

One or more of $R_1$ to $R_{10}$ may independently be one of the monovalent groups represented by Groups (2) to (11), below:

(10)
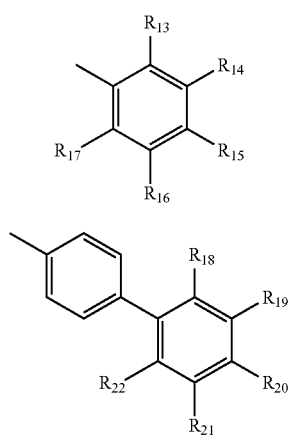

(11)
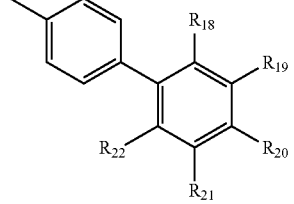

$R_{11}$ to $R_{22}$ may each independently be a hydrogen atom, a halogen atom, an aryl group having 6 to 18 carbon atoms, a hetero aryl group having 6 to 18 carbon atoms, or an alkyl group having 1 to 12 carbon atoms.

$R_1$ may be a phenyl group, a methyl group, or a cyclohexyl group.

Embodiments are also directed to an organic EL material that includes at least one of compounds 1 to 46, below:

Compounds 1 to 46:

1
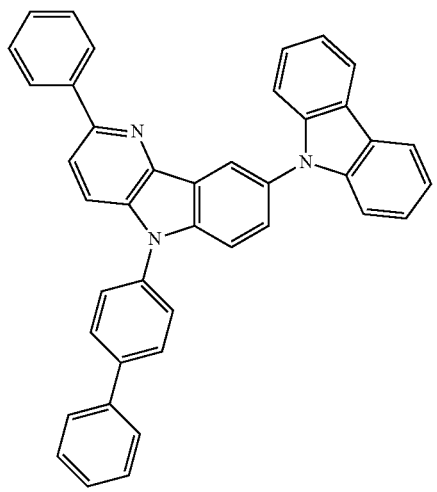

2
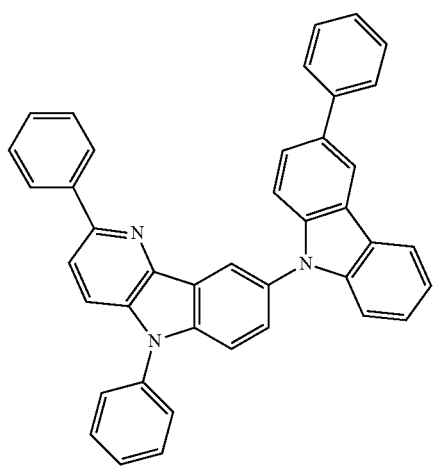

3
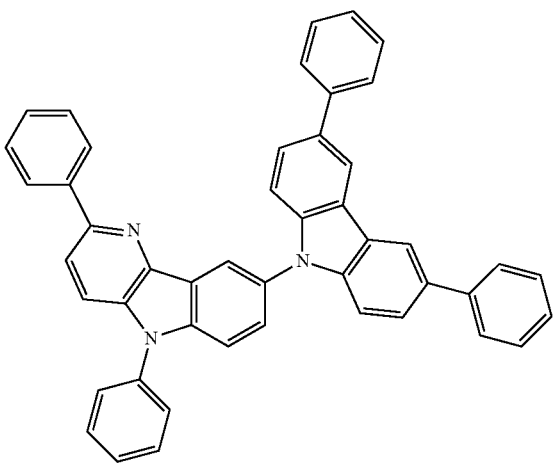

4
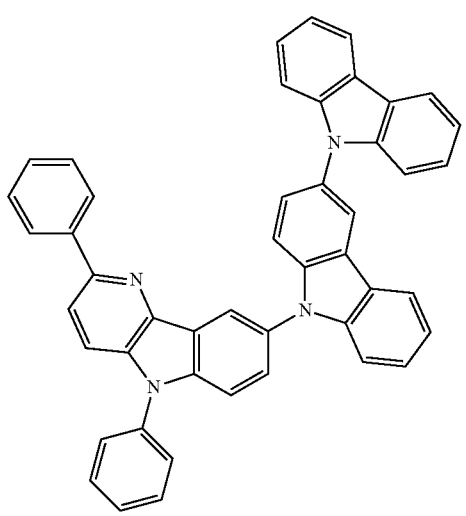

5
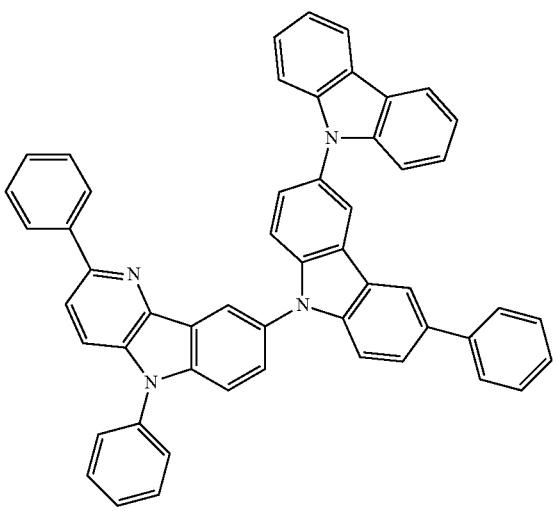

6
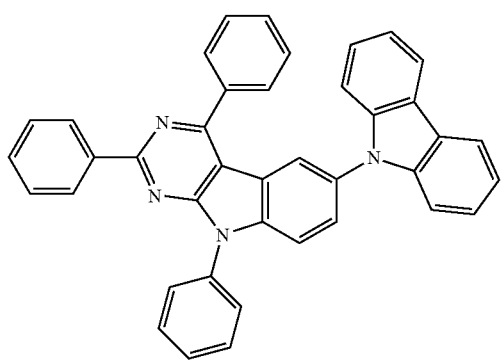
7
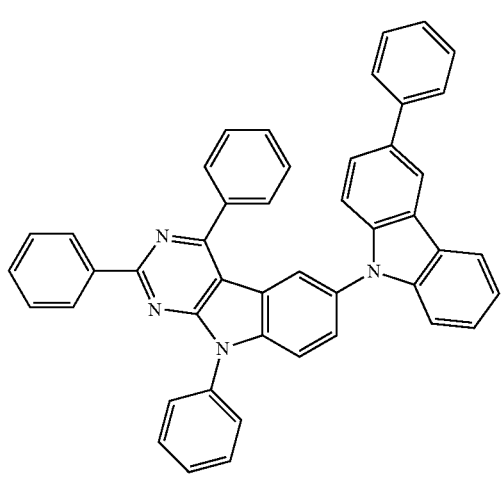 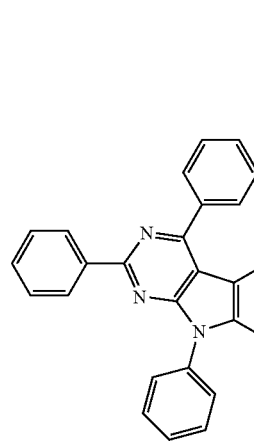
8
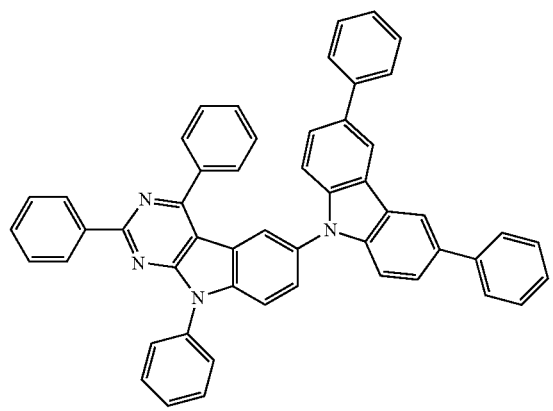
9
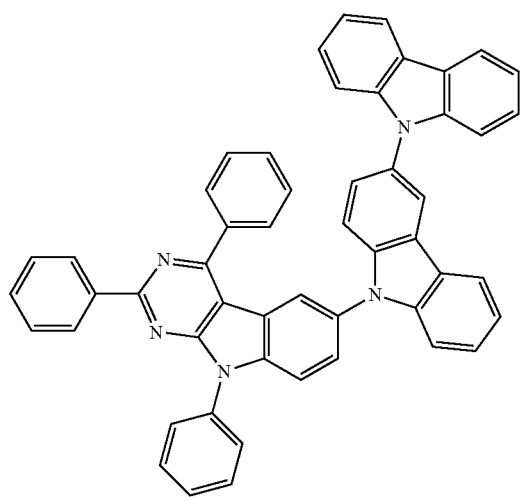
10
11
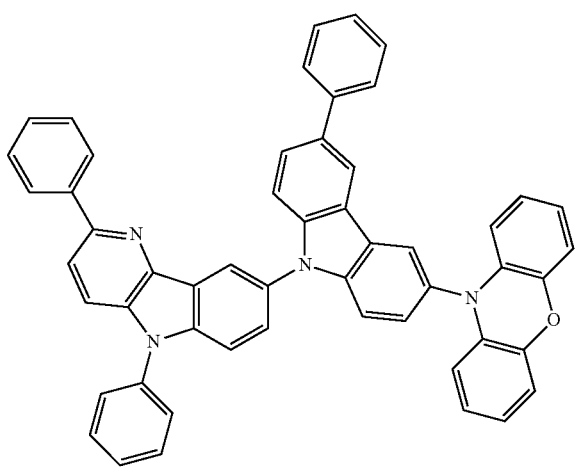

12
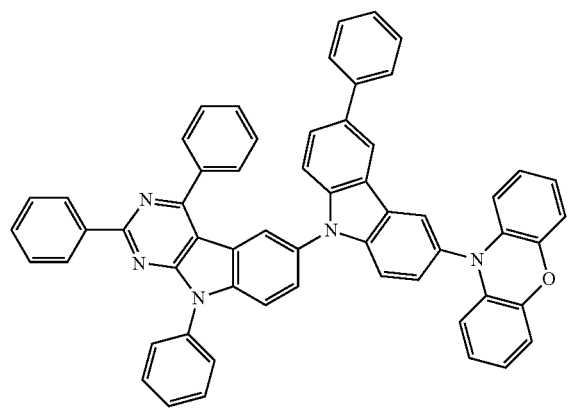
13
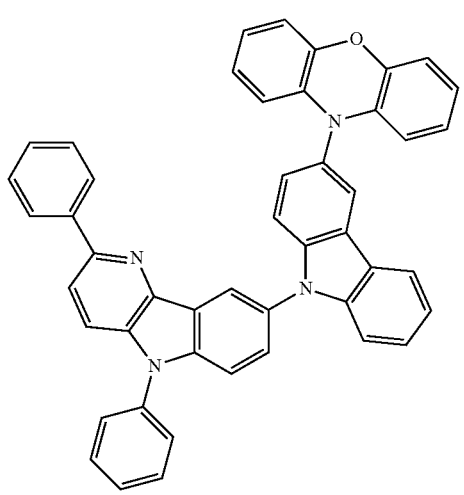
14
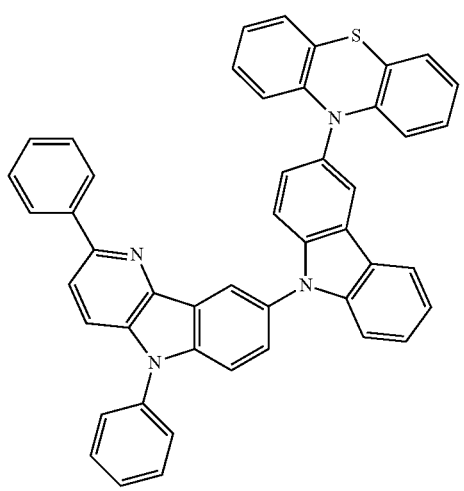
15
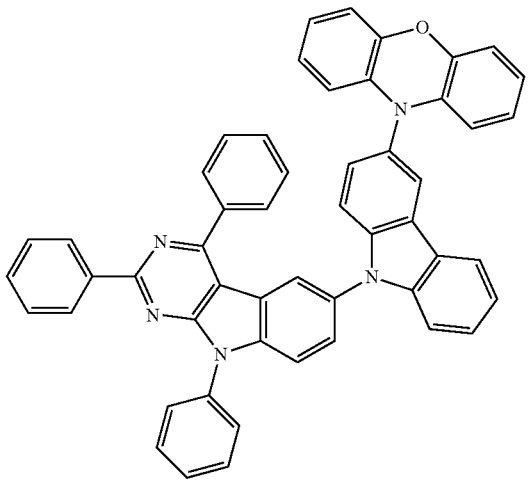
16
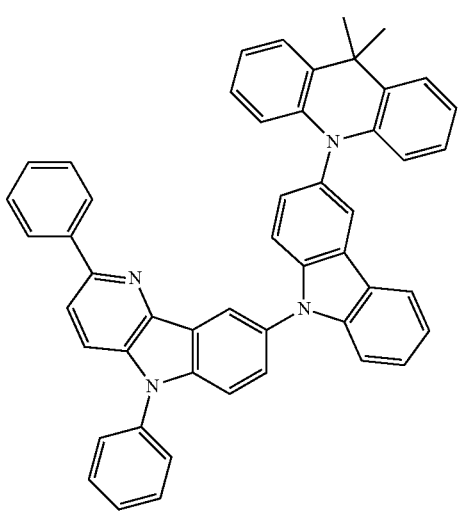
17
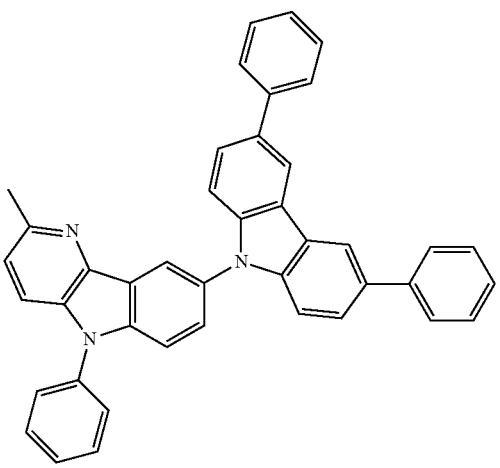

18
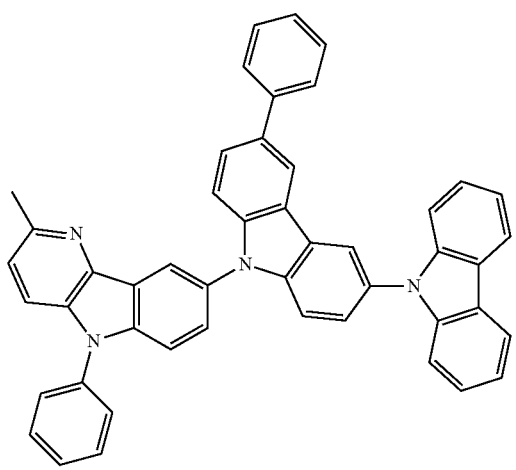
19
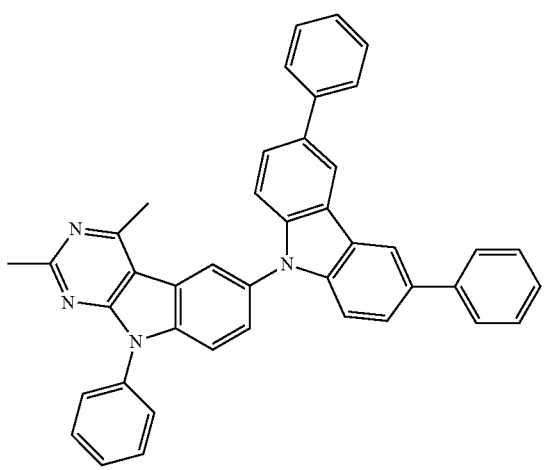
20
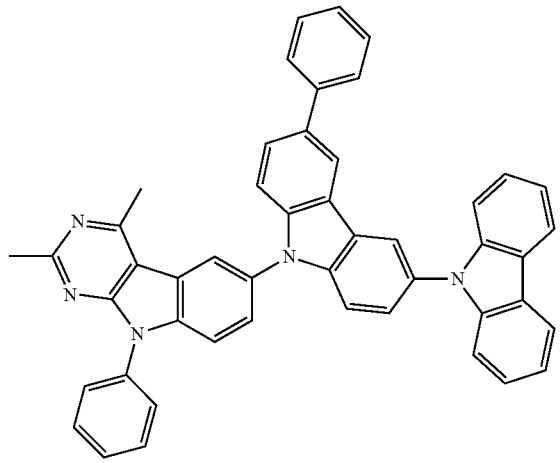
21
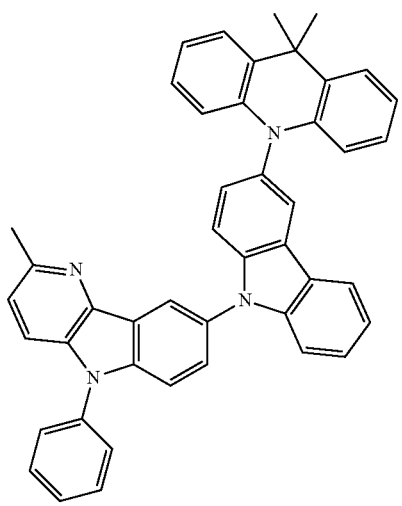
22
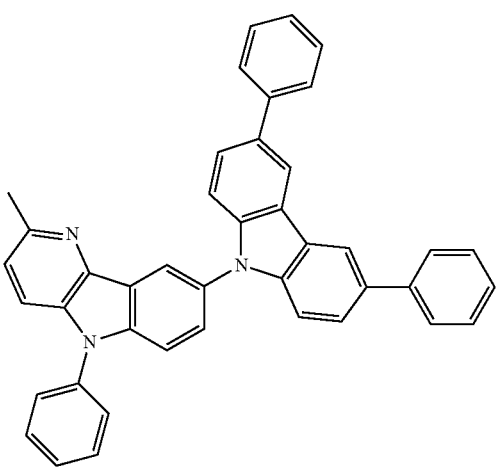
23
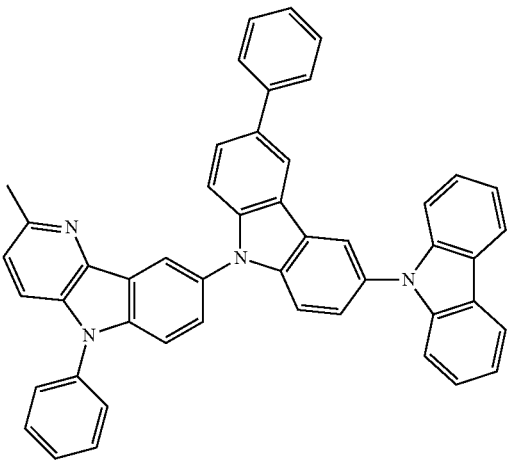

24
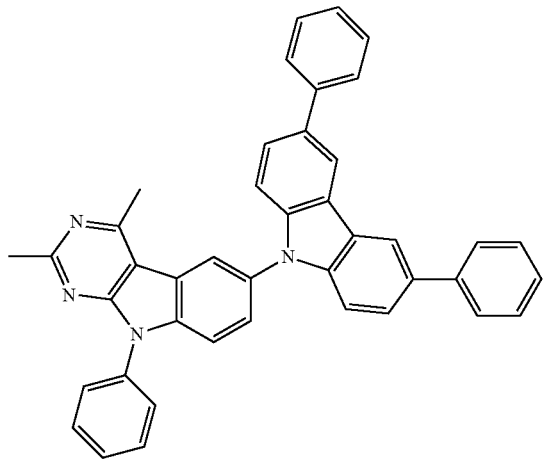
25
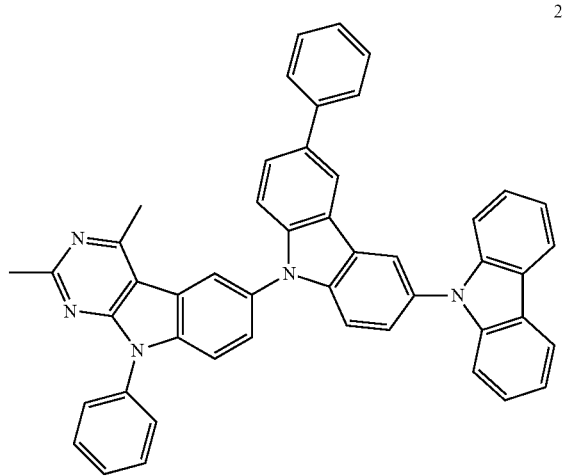
26
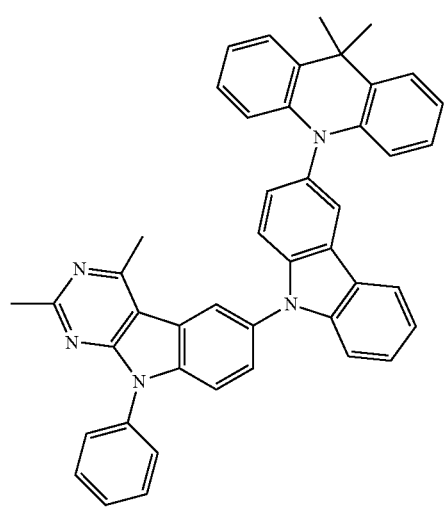
27
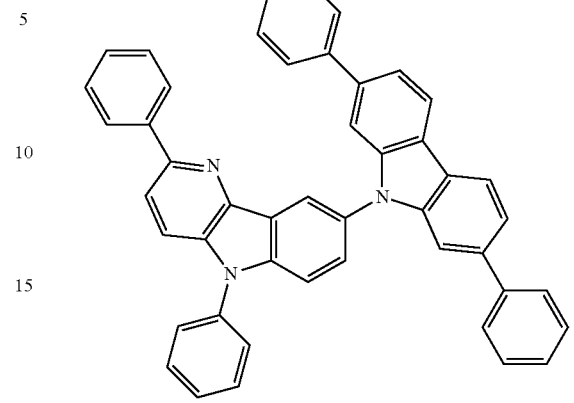
28
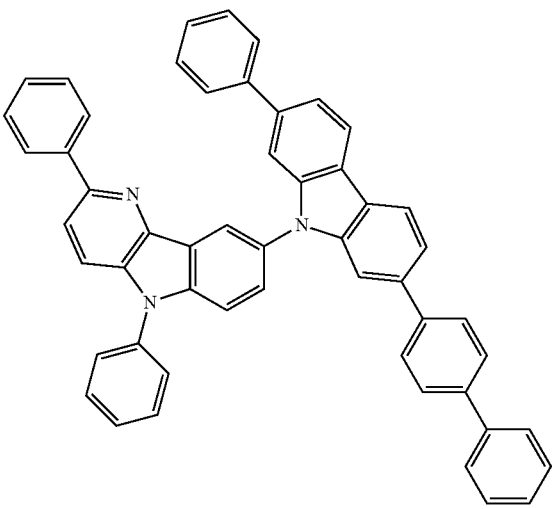
29
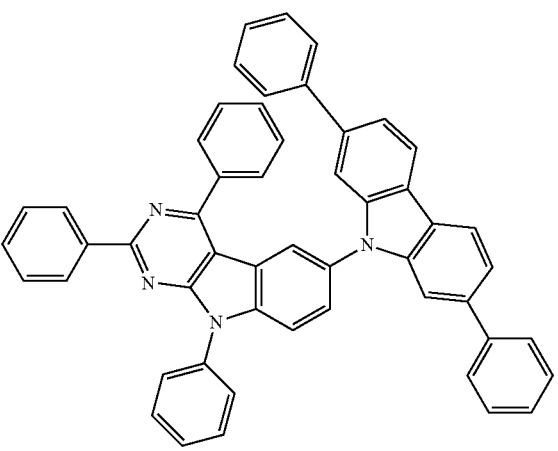

30
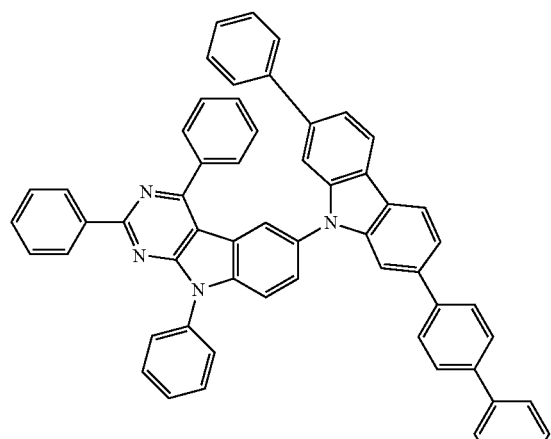
31
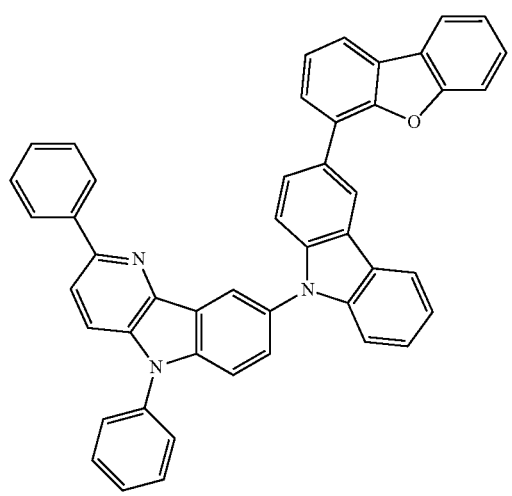
32
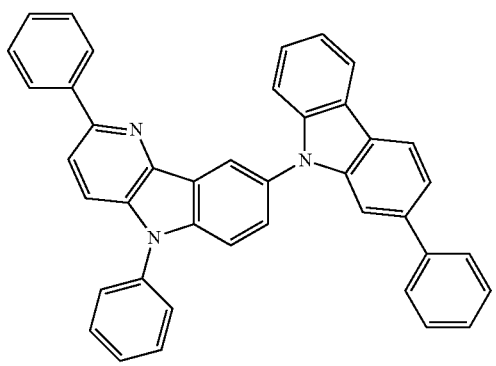
33
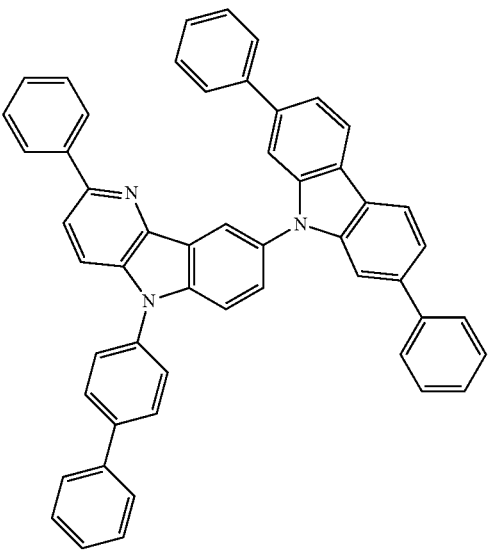
34
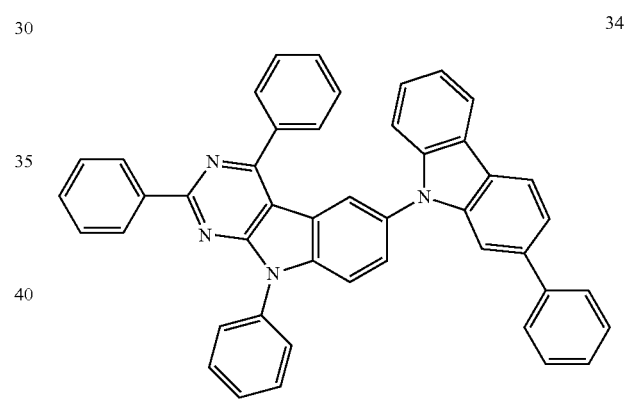
35
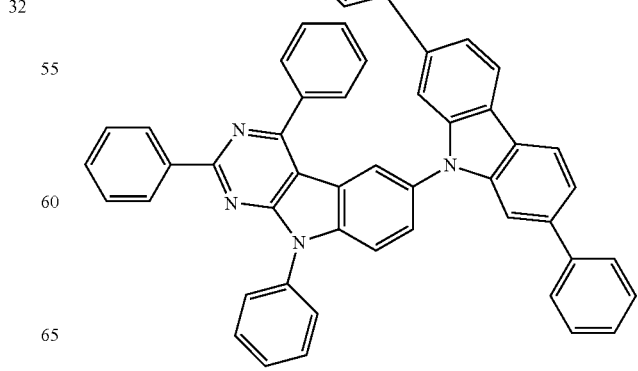

36
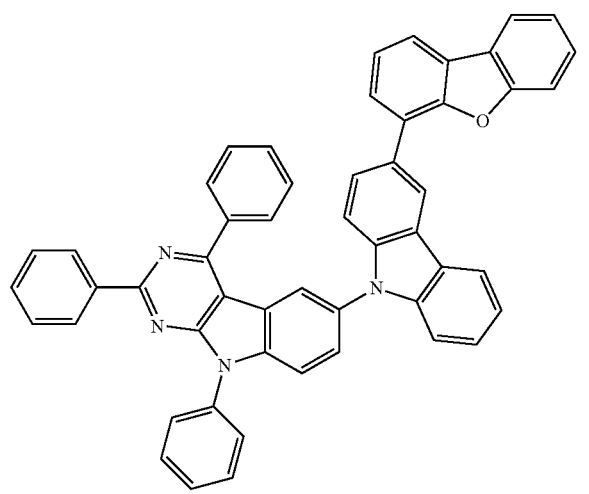
37
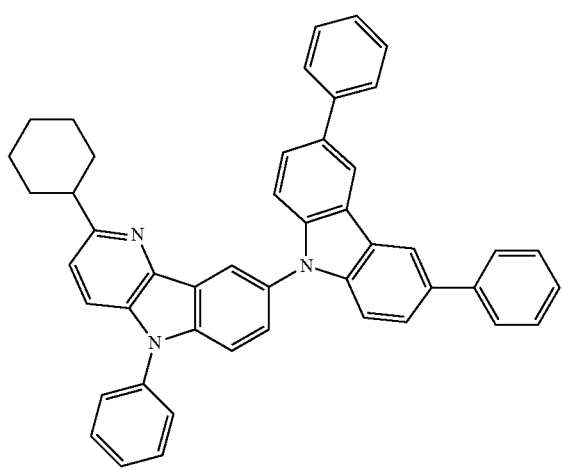
38
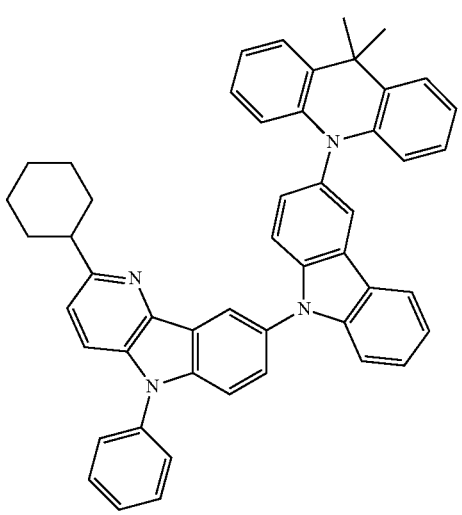
39
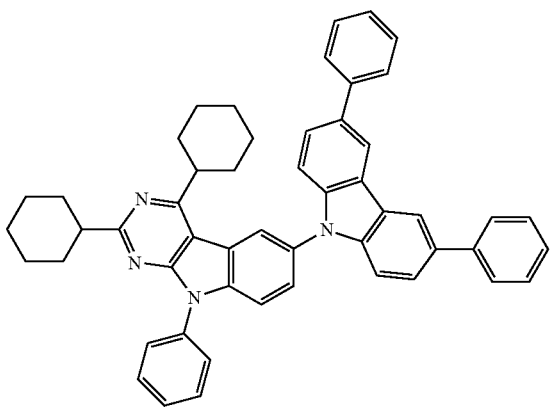
40
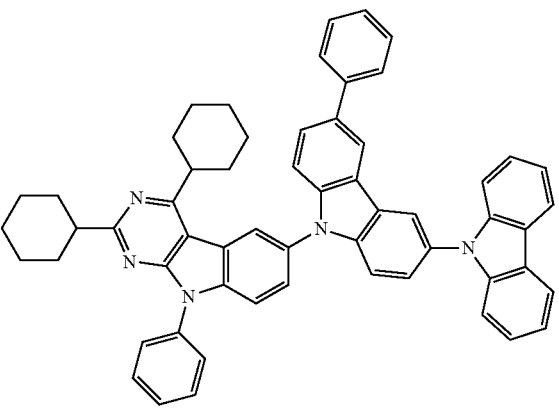
41

42

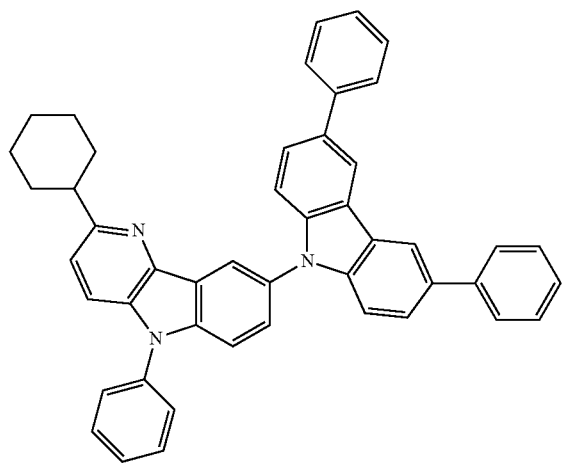

43

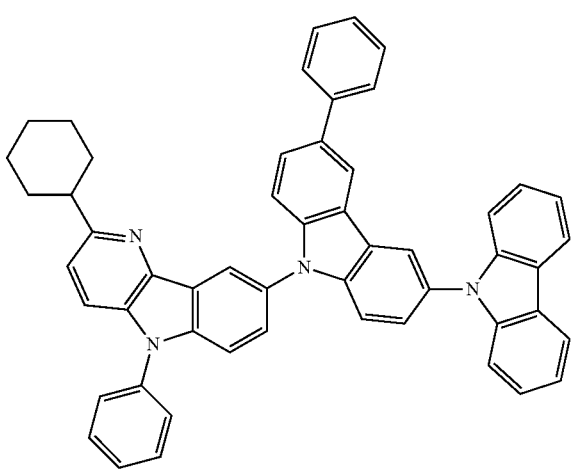

44

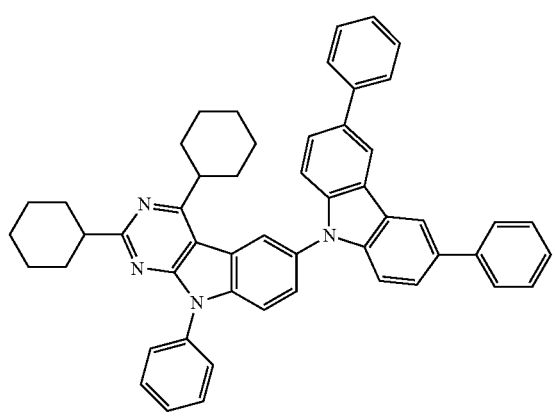

45

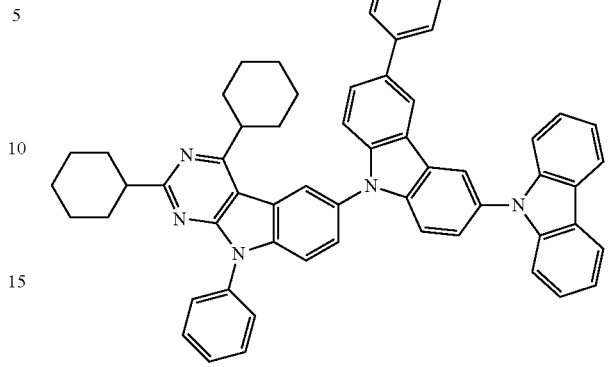

46

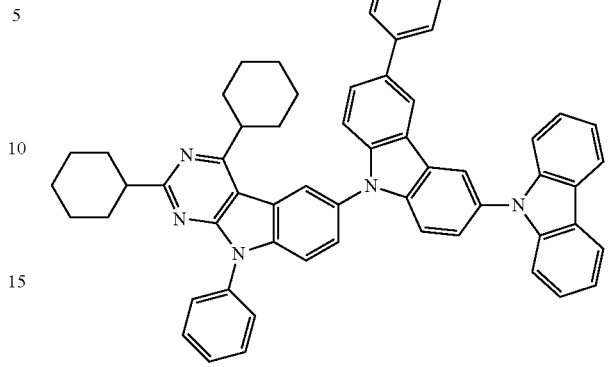

BRIEF DESCRIPTION OF THE DRAWING

Features will become apparent to those of skill in the art by describing in detail exemplary embodiments with reference to the attached drawing in which:

FIG. 1 illustrates a schematic view depicting a structure of an organic EL device.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or substrate, it can be directly on the other layer or substrate, or intervening layers may also be present.

According to embodiments, the luminous efficiency of an organic EL device may be improved and a long life may be realized by using a particular compound, e.g., an azacarbazole derivative having a carbazole group, as a host material in a light-emitting layer of the organic EL device. Hereinafter, an azacarbazole derivative having a carbazole group according to embodiments will be described.

In an implementation, the azacarbazole derivative having a carbazole group that may be used as a host material of a light-emitting layer of an organic EL device may be a compound represented by Formula 1, below:

[Formula 1]

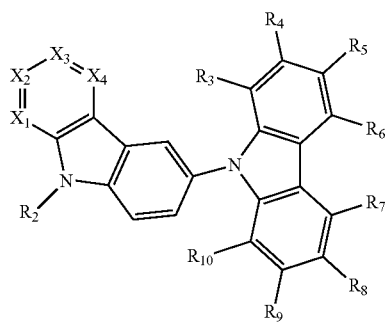

(1)

In Formula 1, $X_1$ to $X_4$ may each be a nitrogen (N) atom or a carbon atom monovalently bonded to a substituent $R_1$ (e.g., C—$R_1$) as further defined. At least one of $X_1$ to $X_4$ may be a nitrogen (N) atom. $R_1$ may be a hydrogen atom, a halogen atom, an aryl group having 6 to 18 carbon atoms, hetero aryl group having 6 to 18 carbon atoms, or an alkyl group having 1 to 12 carbon atoms. In the case where the alkyl group has at least 3 carbon atoms, the alkyl group may be a cycloalkyl group. $R_2$ to $R_{10}$ may each independently be a hydrogen atom, an aryl group having 6-30 carbon atoms or a hetero aryl group having 6-30 carbon atoms.

In an implementation, $R_2$ to $R_{10}$ may be a monovalent group represented by one of Groups (2) to (11), below. (* is a bonding site).

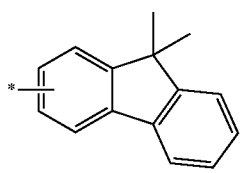

(2)

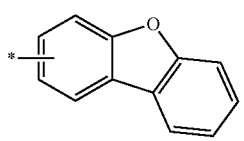

(3)

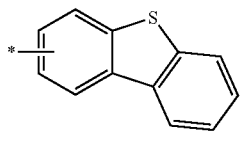

(4)

-continued

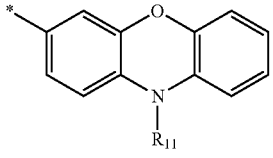

(5)

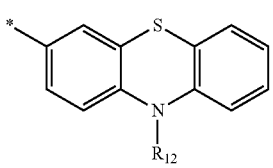

(6)

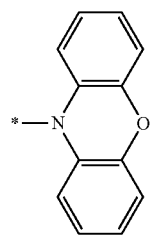

(7)

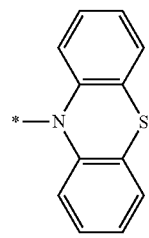

(8)

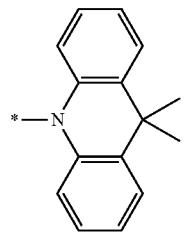

(9)

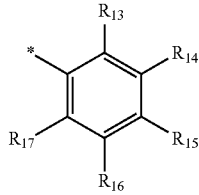

(10)

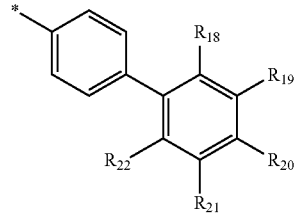

(11)

In groups (2) to (11), $R_{11}$ to $R_{22}$ may each independently be a hydrogen atom, a halogen atom, an aryl group having 6 to 18 carbon atoms, a hetero aryl group having 6 to 18 carbon atoms, or an alkyl group having 1 to 12 carbon atoms.

Generally, a compound having a carbazole group may have electron resistance. Electron resistance and electron transportability may be provided to a compound having a carbazole group by substituting nitrogen for at least one of the carbons, transforming the carbazole ring into an amine compound having a carbazole site exhibiting the hole transportability, the amine compound having an azacarbazole skeleton. The azacarbazole derivative having the carbazole group according to embodiments may have electron transportability as well as hole transportability. Accordingly, the azacarbazole derivative may be used as a host material for a light-emitting layer of an organic EL device, and particularly, may be suitably used as a host material for a phosphorescent light-emitting layer in a green region. The azacarbazole derivative according to embodiments may have having a carbazole group having electron resistance and an azacarbazole group. Accordingly, the azacarbazole derivative may contribute to improvement of electron resistance and long life of an organic EL device. Also, the electron transportability in the azacarbazole derivative having a carbazole group according to embodiments may be improved by the azacarbazole group. Accordingly, the luminous efficiency of an organic EL device may be improved.

In an azacarbazole derivative having a carbazole group according to an embodiment, the number of nitrogen (N) atoms contained in an azacarbazole ring may be 1 or 2. In Formula 1, one or two of $X_1$ to $X_4$ may be a nitrogen (N) atom. In an azacarbazole derivative having a carbazole group according to embodiments, the electron density of carbon (C) atoms adjacent to the nitrogen atom of the azacarbazole ring may be increased. The substituent $R_1$, which is monovalently bonded to a carbon (C) atom adjacent to the nitrogen atom of the azacarbazole ring, may be a phenyl group. The nitrogen (N) atom of the azacarbazole ring may have a strong electron withdrawing property. Accordingly, it may be possible to improve the electron resistance by introducing a phenyl group having a higher electron resistance than a hydrogen atom or the like onto a carbon (C) atom adjacent to the nitrogen atom of the azacarbazole ring. Also, $R_1$ which is monovalently bonded to the carbon (C) atom adjacent to the nitrogen atom of the azacarbazole ring, may be an alkyl group, for example, a methyl group, which may cause less vibration in molecules and for which it may be difficult to contribute to non-radiation and non-activation. In other implementations, a cycloalkyl group, for example, a cyclohexyl group, which may cause less vibration in molecules and for which it may be difficult to contribute to non-radiation and non-activation, may be used as $R_1$.

Also, in an implementation, at least one of $R_2$ to $R_{10}$ in a compound represented by Formula 1 may be a monovalent group represented by group 10 or group 11, above. In an implementation, the azacarbazole derivative having a carbazole group in which at least one of $R_2$ to $R_{10}$ is a monovalent group represented by group 11 or group 12 has a reduced HOMO (highest occupied molecular orbital) level. Accordingly, injection of holes into the light-emitting layer may be made easier. Therefore, the azacarbazole derivative having a carbazole group in which at least one of $R_2$ to $R_{10}$ is a monovalent group represented by group 11 or group 12 may be particularly suitable for a host material of a light-emitting layer of an organic EL device.

Compounds (1) to (46), which are examples of azacarbazole derivatives having a carbazole group according to embodiments, are shown below.

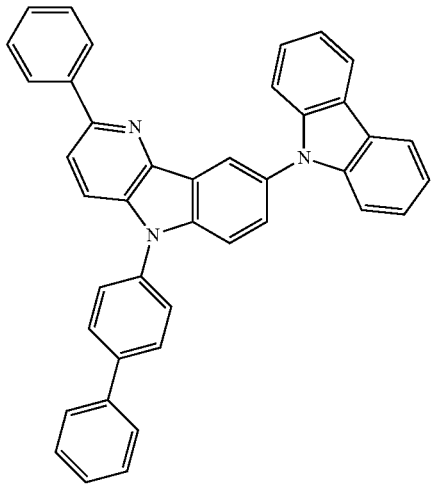

1

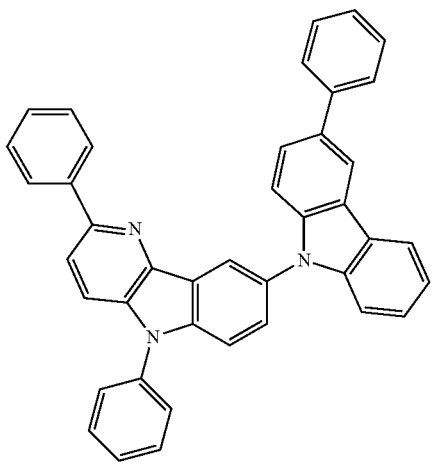

2

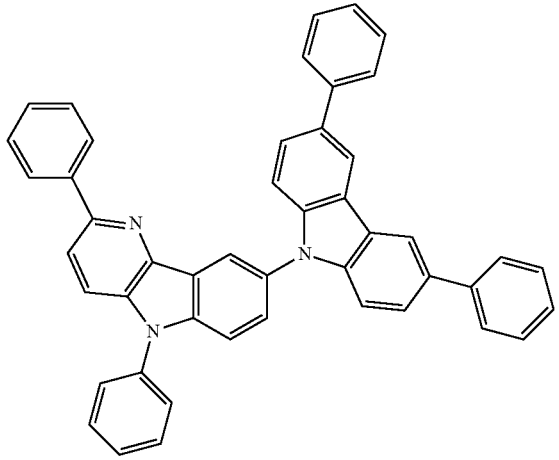

3

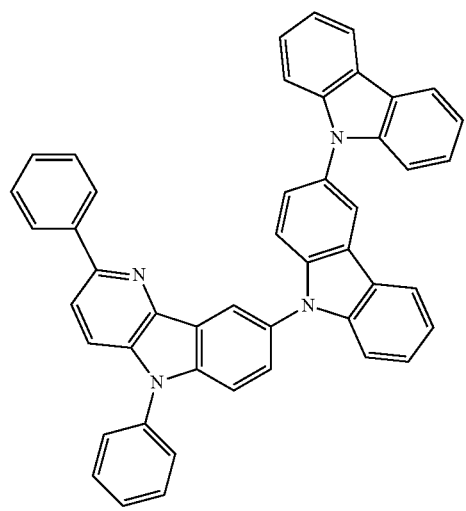
4
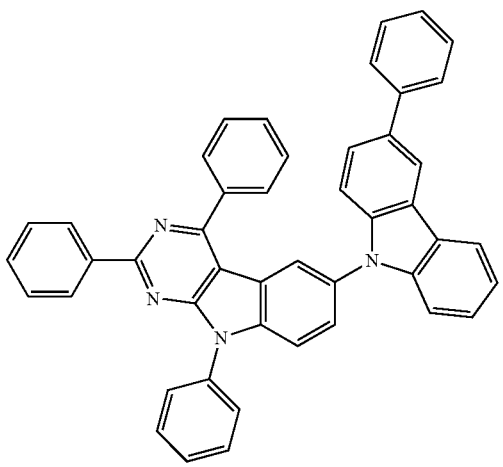
7
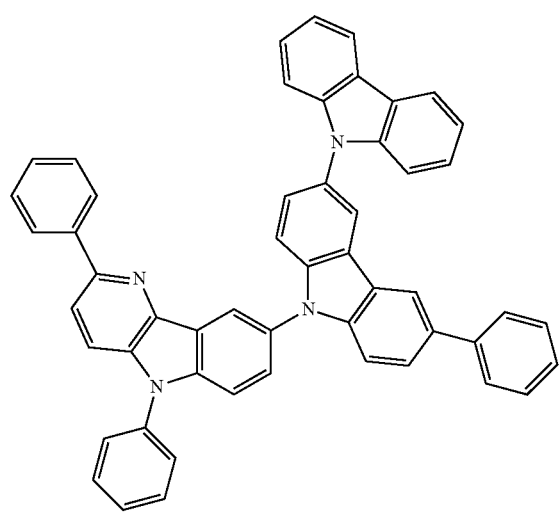
5
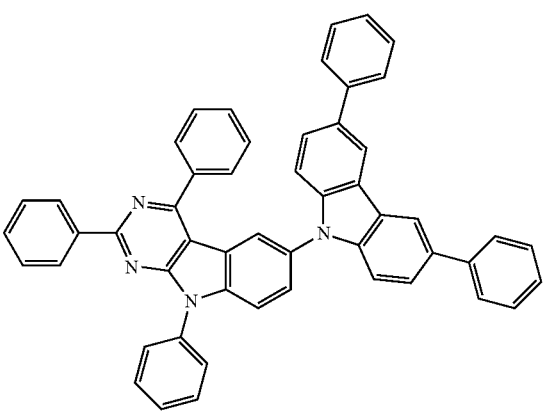
8
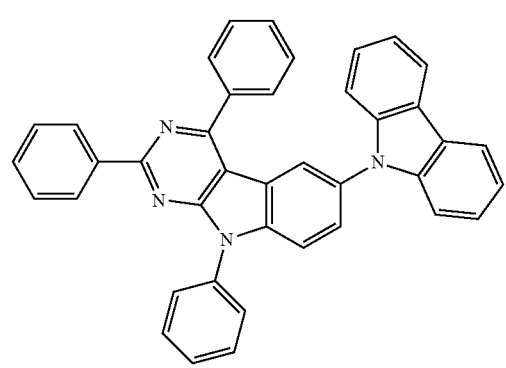
6
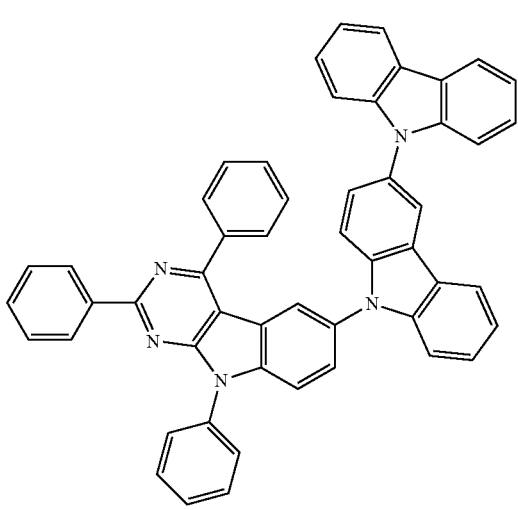
9

10
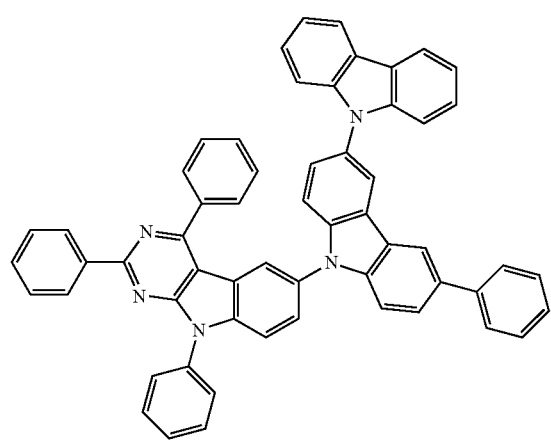
13
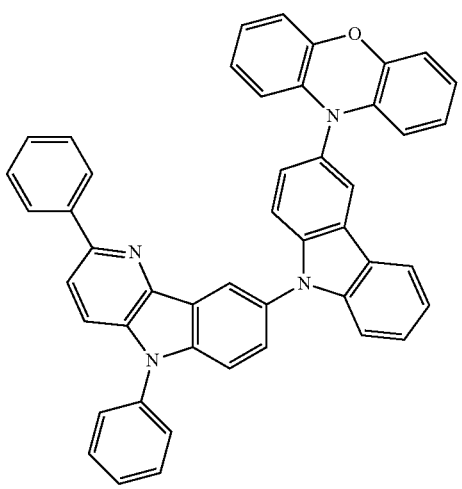
11
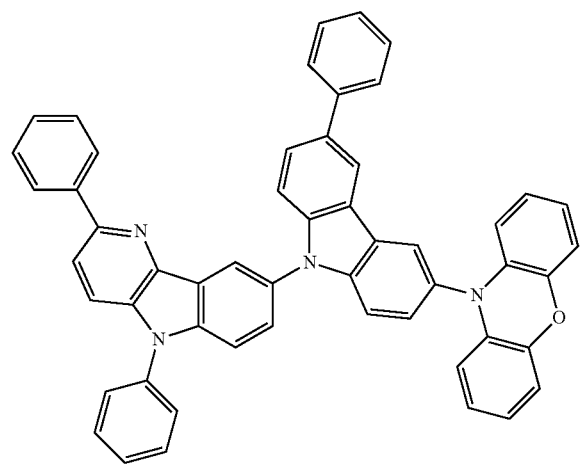
14
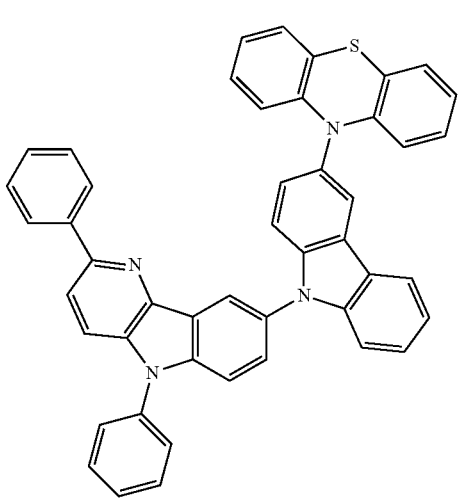
12
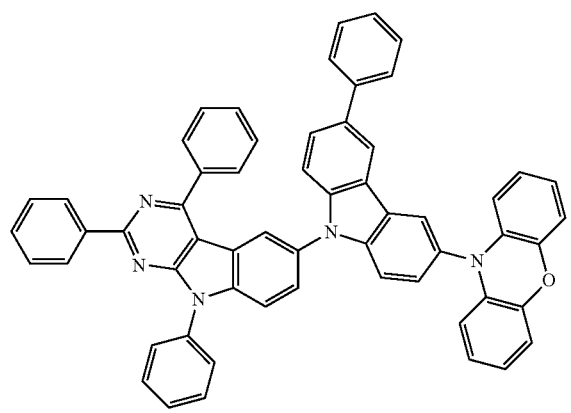
15
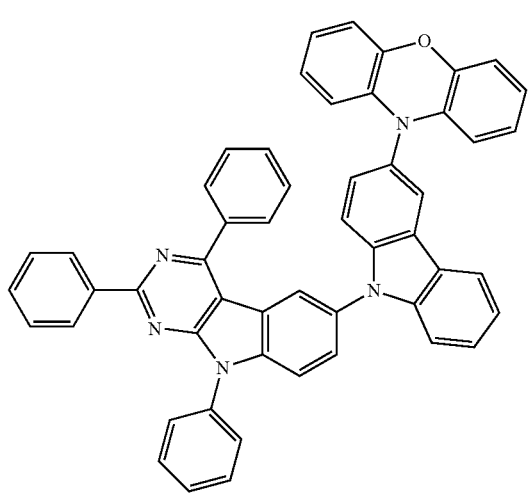

16
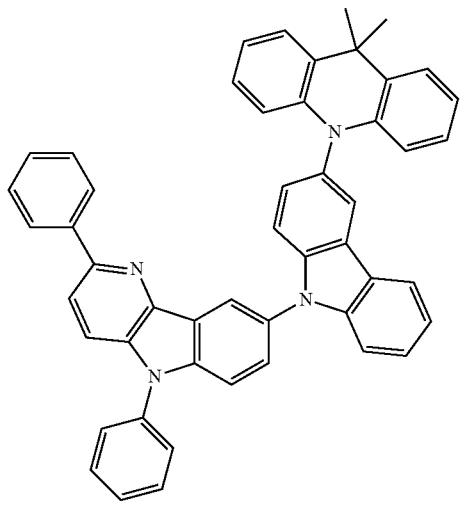
17
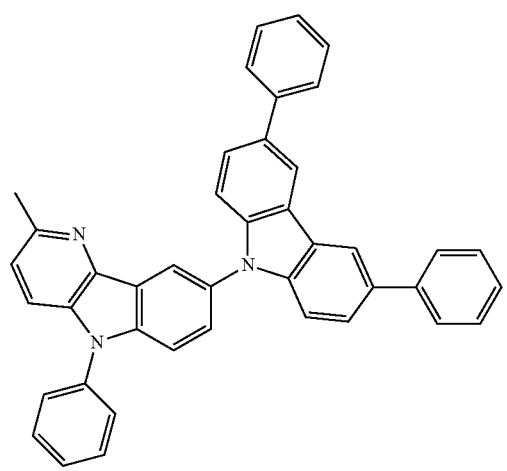
18
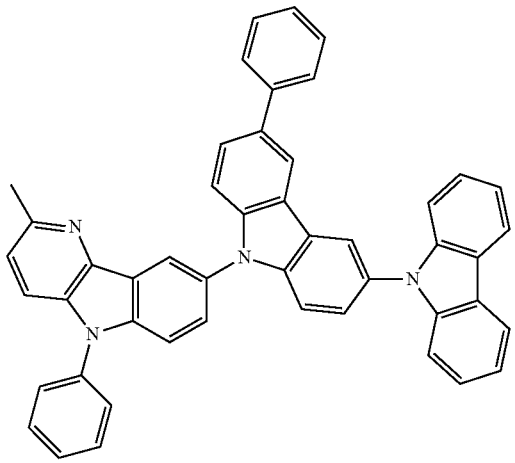
19
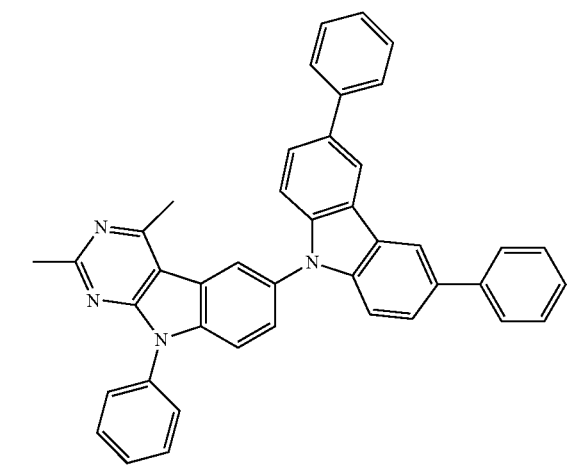
20
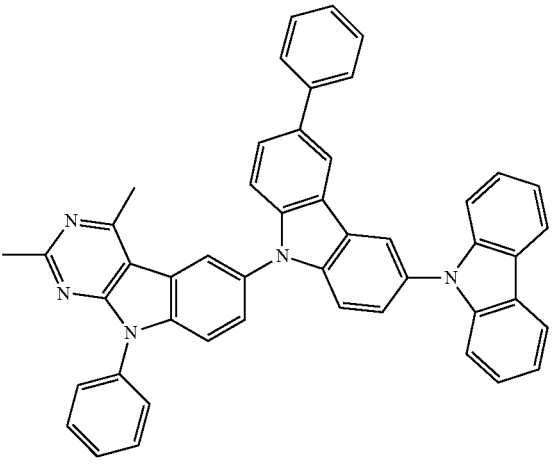
21
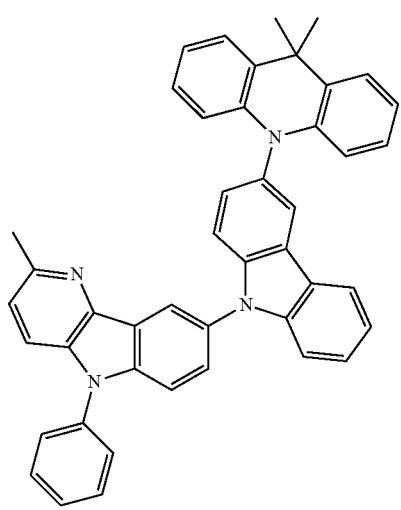

22
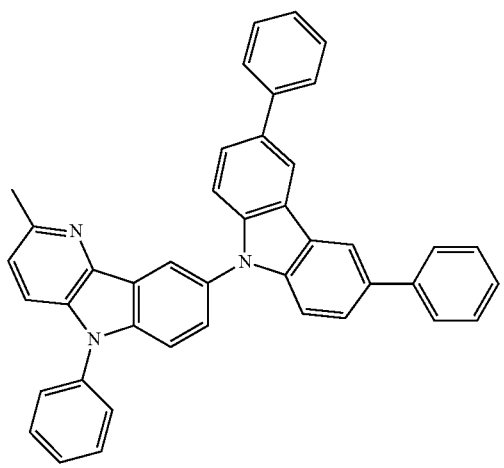
23
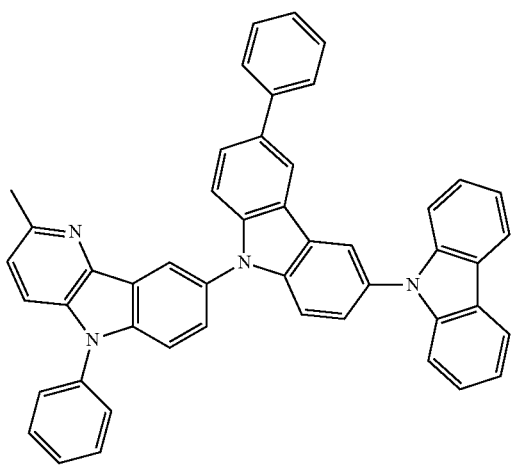
24
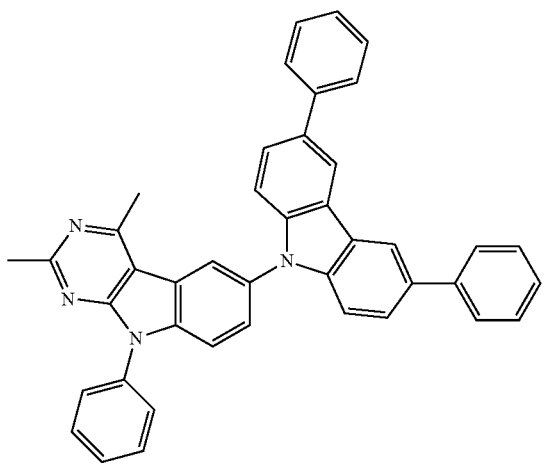
25
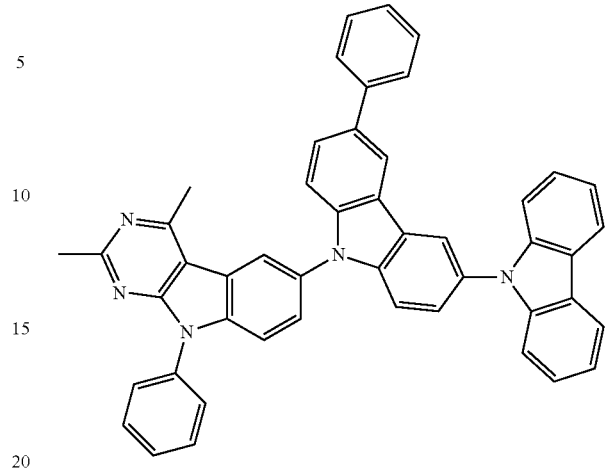
26
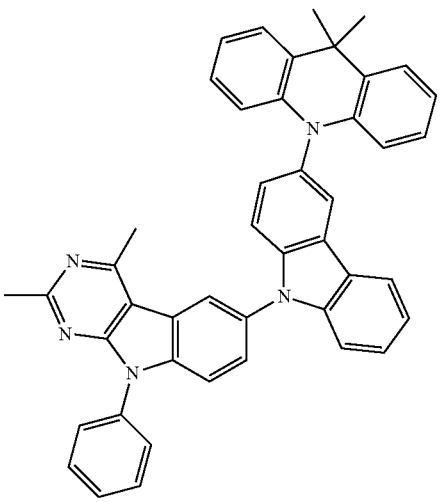
27
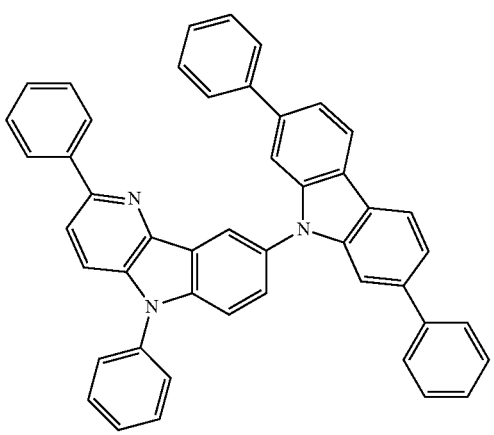

33
-continued
28
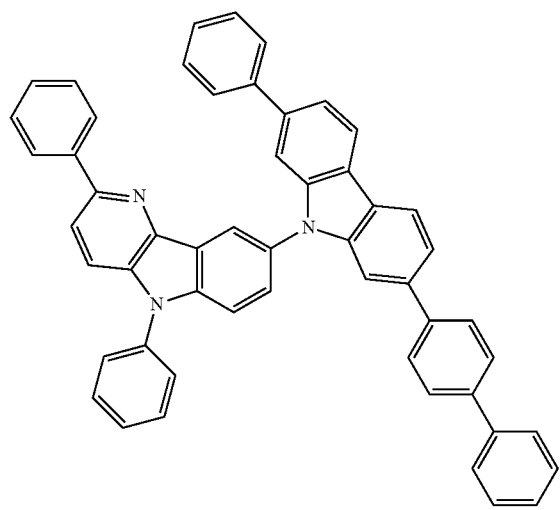
29
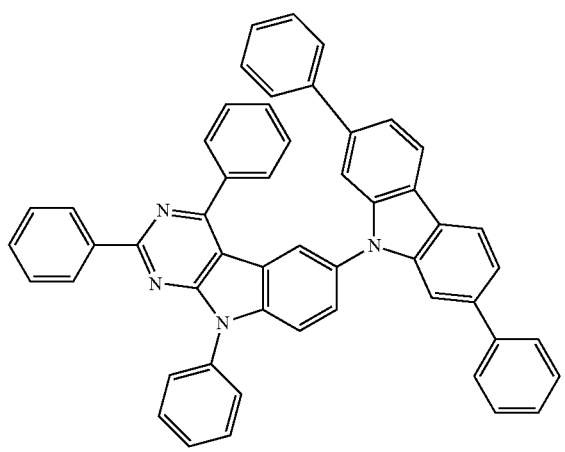
30
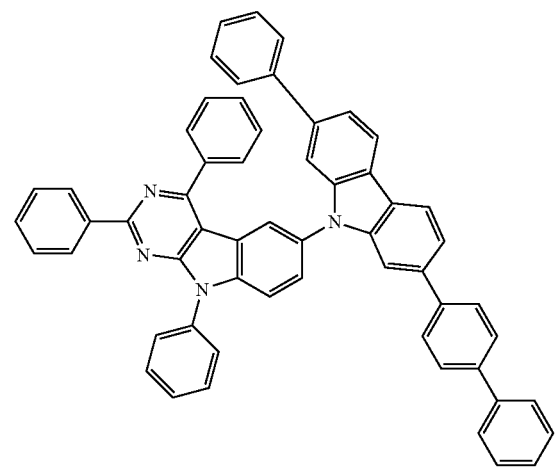
34
-continued
31
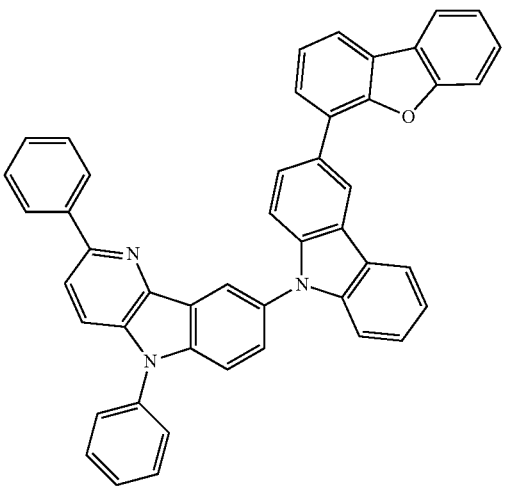
32
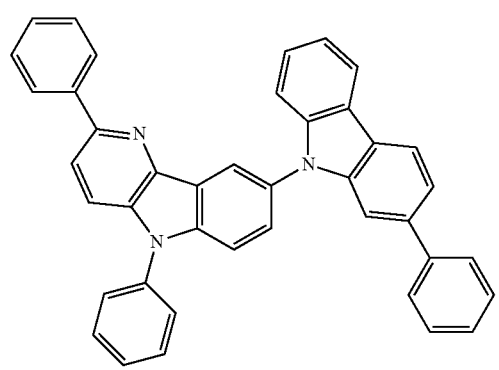
33
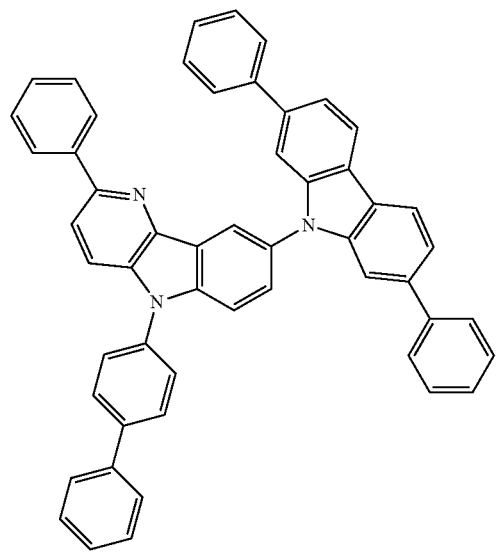

34
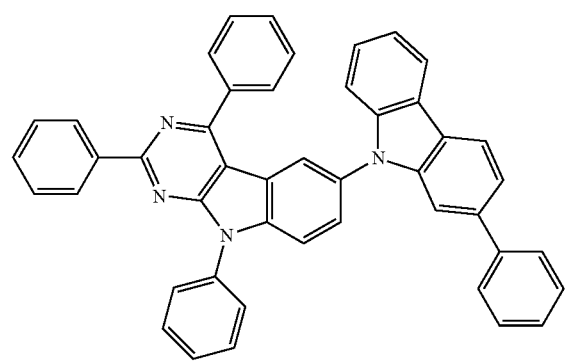
35
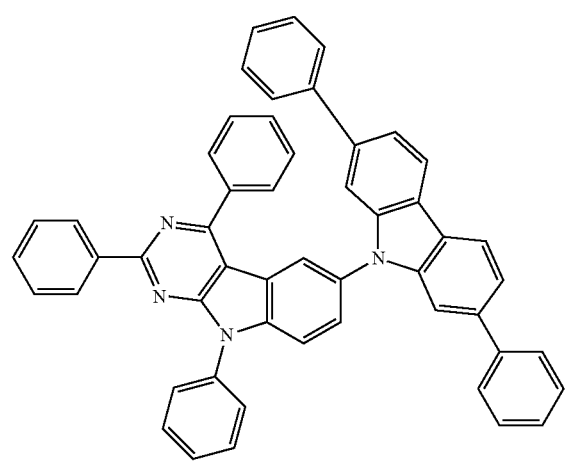
36
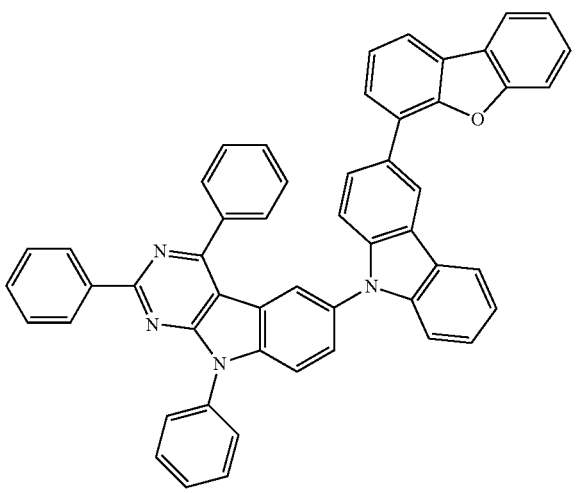
37
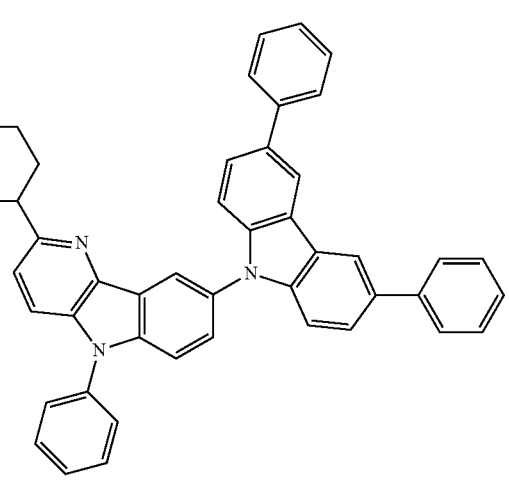
38
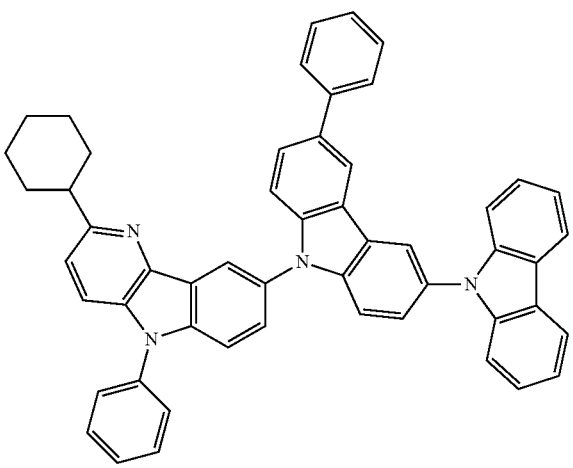
39
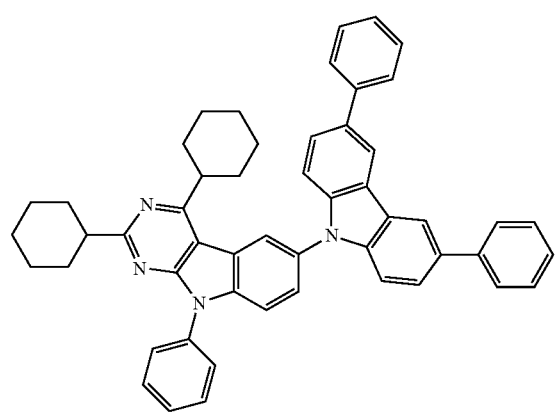

40
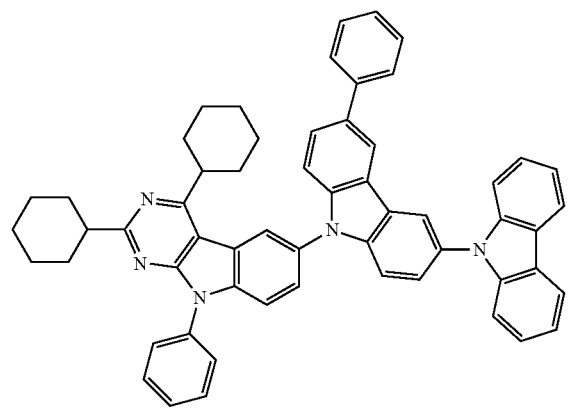
41
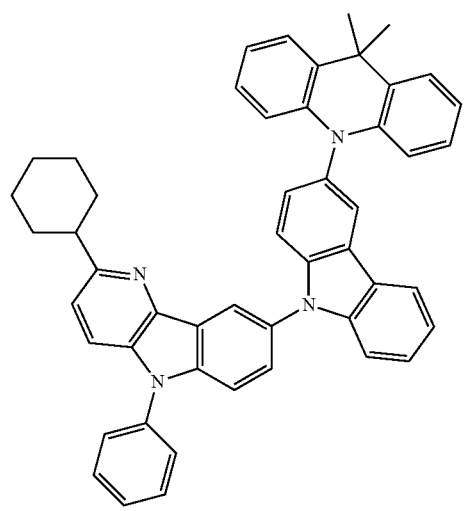
42
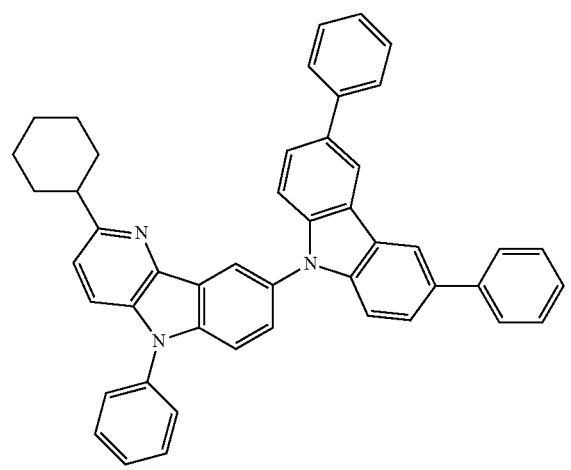
43
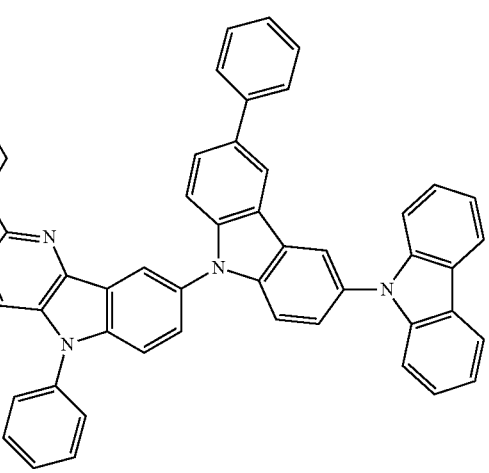
44
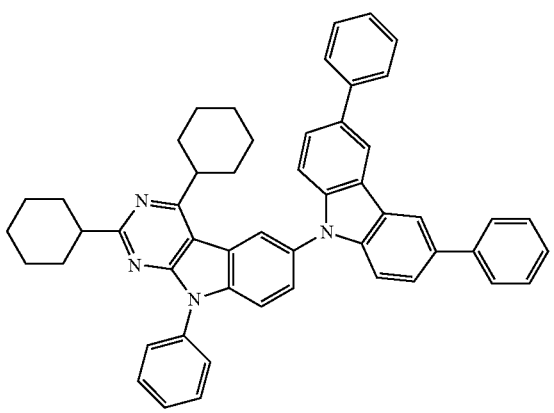
45
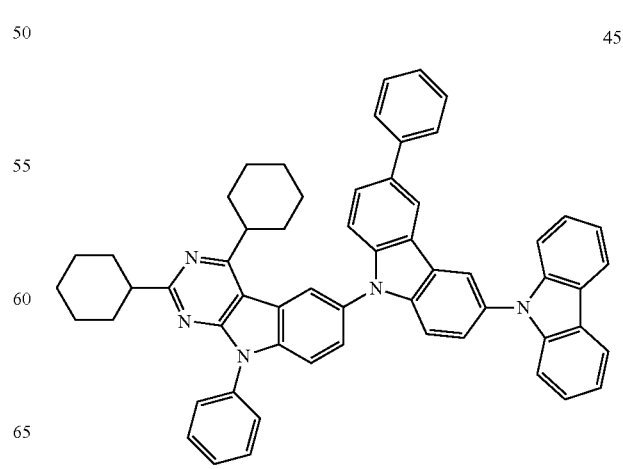

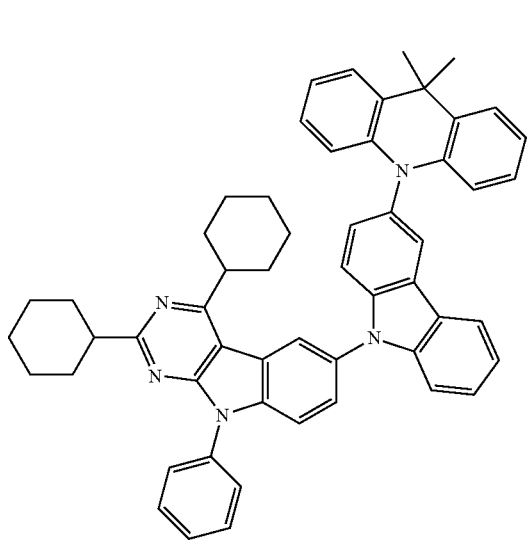

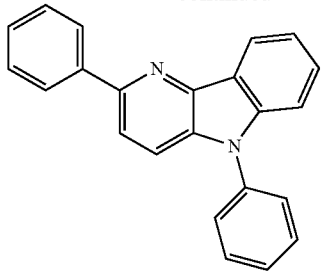

C (71%)

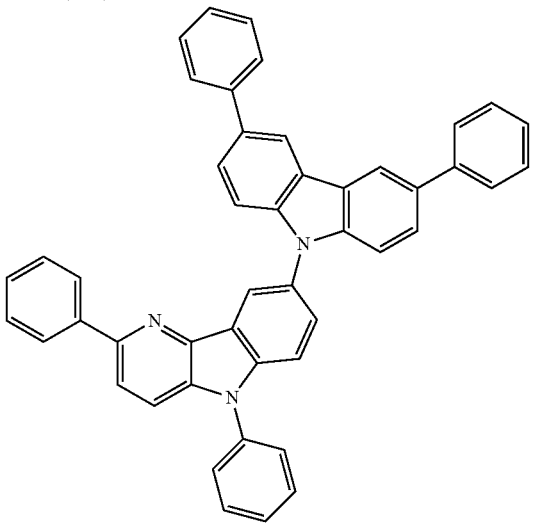

D (95%)

The following Examples and Comparative Examples are provided in order to highlight characteristics of one or more embodiments, but it is to be understood that the Examples and Comparative Examples are not to be construed as limiting the scope of the embodiments, nor are the Comparative Examples to be construed as being outside the scope of the embodiments. Further, it is to be understood that the embodiments are not limited to the particular details described in the Examples and Comparative Examples.

A example of a method of synthesizing the above-described compound 3, which is one of the azacarbazole derivatives having a carbazole group, will be described below with reference to Reaction Scheme 1, below.

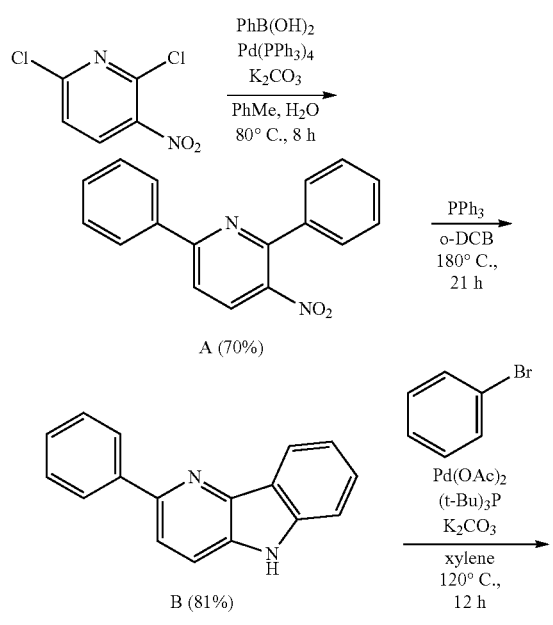

Synthesis of Compound A 5.00 g of 2,6-dichloro-3-nitropyridine, 9.48 g of phenylboronic acid (PhB(OH)$_2$), 1.34 g of tetrakis(triphenylphosphine)palladium (Pd(PPh$_3$)$_4$), 10.7 g of potassium carbonate, 20 mL of water, and 10 mL of ethanol were added in a 300 mL three-necked flask under an argon atmosphere, and the mixture was stirred at 80° C. for 8 hours in 100 mL of a toluene solvent. The mixture was cooled in the air, an organic layer was separated, and the solvent was removed by distillation. The remaining mixture was again precipitated by using a dichloromethane/methanol solvent to obtain 4.31 g of yellow solid compound A (yield: 70%).

Compound A was identified through $^1$H-NMR and FAB-MS. Compounds B, C, and 3 described below were also identified by $^1$H-NMR and FAB-MS. Compound D was identified by $^1$H-NMR and LC-MS. In the $^1$H-NMR measurement, CDCl$_3$ was used as a solvent.

Chemical shift values of compound A measured by ¹H-NMR were 8.22 (d, 1H), 8.11-8.14 (m, 2H), 7.82 (d, 1H), 7.64 to 7.68 (m, 2H), and 7.47 to 7.52 (m, 6H). The molecular weight of compound A measured by FAB-MS was 277.

Synthesis of Compound B 3.80 g of compound A and 9.02 g of triphenylphosphine (PPh₃) were added in a 50 mL two-necked flask under an argon atmosphere, and the mixture was stirred at 80° C. for 8 hours in 30 mL of an o-dichlorobenzene solvent. The mixture was cooled in air, an organic layer was separated by adding water, and the solvent was removed by distillation. The obtained crude product was purified by silica gel column chromatography (a mixed solvent of dichloromethane and hexane), and was then recrystallized by a mixed solvent of dichloromethane and ethanol to obtain 2.72 g of yellow solid compound B (yield: 81%).

Chemical shift values of compound B measured by ¹H-NMR were 9.39 (s, 1H), 8.44 (d, 1H), 8.38 (d, 1H), 8.14 (d, 1H), 7.97 (d, 1H), 7.69 to 7.71 (m, 4H), and 7.44 (d, 2H). The molecular weight of compound B measured by FAB-MS was 245.

Synthesis of Compound C 2.80 g of compound B, 1.59 mL of bromobenzene, 22.8 mg of palladium (II) acetate (Pd(OAc)₂), 30.5 mg of tri-tert-butylphosphine ((t-Bu)₃P), and 4.20 g of potassium carbonate (K₂CO₃) were added in a 50 mL two-necked flask under an argon atmosphere. The mixture was stirred at 80° C. for 8 hours in 30 mL of an o-dichlorobenzene solvent, and the mixture was heated and stirred at 120° C. for 12 hours in 30 mL of a xylene solvent. The mixture was cooled in air, an organic layer was separated by adding water, and the solvent was removed by distillation. The obtained crude product was purified by silica gel column chromatography (a mixed solvent of chloroform and hexane), and was then recrystallized by a mixed solvent of dichloromethane and hexane to obtain 2.31 g of yellow solid compound C (yield: 71%).

Chemical shift values of compound C measured by ¹H-NMR were 8.41 (q, 1H), 8.14 (d, 2H), 7.80 (q, 2H), 7.44 to 7.71 (m, 4H), 7.31 to 7.43 (m, 5H), 7.43 (d, 2H), and 7.34 (d, 2H). The molecular weight of compound C measured by FAB-MS was 321.

Synthesis of Compound D 1.16 g of compound C and 0.64 g of N-bromosuccinimide (NBS) were added to a 50 mL of two-necked flask, and the mixture was stirred at room temperature for 24 hours in an acetic acid solvent. The mixture was cooled in air, an organic layer was separated by adding water, and the solvent was removed by distillation. The obtained crude product was recrystallized by a mixed solvent of dichloromethane and hexane to obtain 1.37 g of yellow solid compound D (yield: 95%).

Chemical shift values of compound D measured by ¹H-NMR were 8.65 (q, 1H), 8.14 (d, 2H), 7.79 (q, 2H), 7.44 to 7.70 (m, 3H), 7.29 to 7.40 (m, 5H), 7.43 (d, 2H), and 7.34 (d, 2H). The molecular weight of compound D measured by LC-MS was 399, 401.

Synthesis of Compound 3

2.00 g of compound D, 1.76 g of 3,6-diphenyl-9H-carbazole, 1.1 mg of palladium (II) acetate (Pd(OAc)₂), 3.0 mg of tri-tert-butylphosphine ((t-Bu)₃P), and 2.08 g of potassium carbonate (K₂CO₃) were added in a 100 mL three-necked flask under an argon atmosphere, and the mixture was heated and stirred at 120° C. for 12 hours in 50 mL of a xylene solvent. The mixture was cooled in air, an organic layer was separated by adding water, and the solvent was removed by distillation. The obtained crude product was purified by silica gel column chromatography (using a mixed solvent of chloroform and hexane), and was then recrystallized by a mixed solvent of toluene and hexane to obtain 2.01 g of white solid compound 3 (yield: 63%)

Chemical shift values of compound 3 measured by ¹H-NMR were 8.75 (d, 1H), 8.44 (d, 2H), 8.16 (q, 2H), 7.84 (q, 2H), 7.67 to 7.76 (m, 12H), 7.46 to 7.57 (m, 9H), and 7.32 to 7.46 (m, 3H). The molecular weight of compound 3 measured by FAB-MS was 638.

EXAMPLES

Current efficiency and half-life of an organic EL device which used an azacarbazole derivative having a carbazole according to embodiments as a host material of a green phosphorescent light-emitting layer were measured. As a host material of a light-emitting layer of an organic EL device, compounds 3, 16, and 4, shown below, were used.

For comparison, comparative compound 1, shown below, was used as a host material of a light-emitting layer of an organic EL device.

3

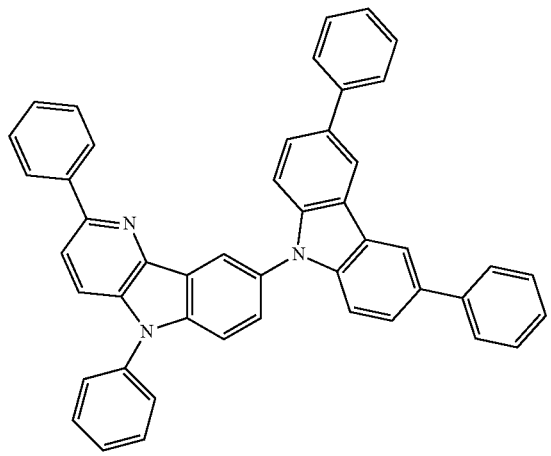

16

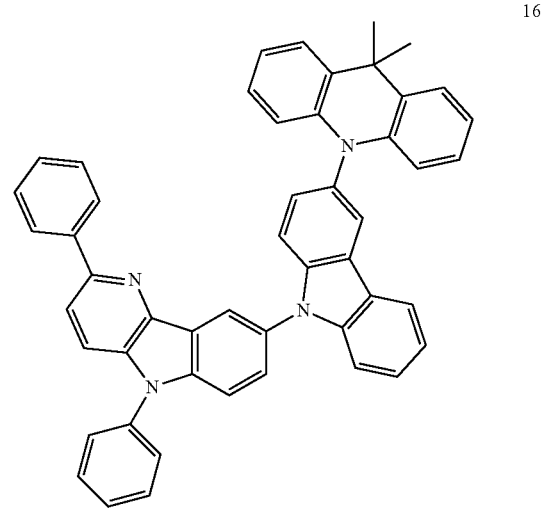

4

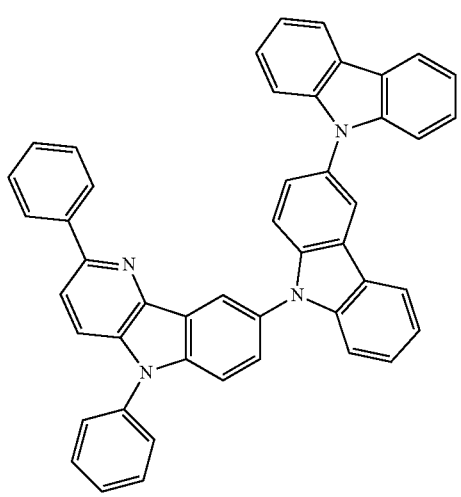

[Comparative compound 1]

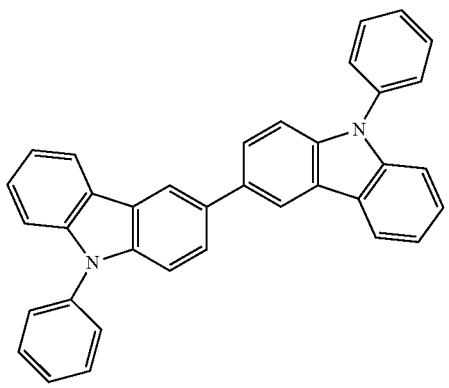

FIG. 1 illustrates a structure of an organic EL device used for measurement. Referring to FIG. 1, an organic EL device 100 illustrated in FIG. 1 included a glass substrate 102, an anode 104 disposed on the glass substrate 102 and formed of indium tin oxide (ITO), a hole injection layer 106 disposed on the anode 104 and including 1-TNATA(4,4'',4''-tris(N-(1-naphthyl)-N-phenylamino)triphenylamine, a hole transport layer 108 disposed on the hole injection layer 106 and including 4,4'-bis[N,N'-(3-tolyl)amino]-3,3'-dimethylbiphenyl (HMTPD), a light-emitting layer 110 disposed on the hole transport layer 108, including any one of the above-described compounds 1, 16 and 4, and comparative compound 1 in a host material, and doped with tris(2-phenylpyridinate)iridium (III) (Ir(ppy)$_3$) to a concentration of 20%, an electron transport layer 112 disposed on the light-emitting layer 110 and including Alq$_3$, an electron injection layer 114 disposed on the electron transport layer 112 and including LiF, and a cathode 116 disposed on the electron injection layer 114 and formed of aluminum (Al). The anode 104 was 150 nm thick, the hole injection layer 106 was 60 nm thick, the hole transport layer 108 was 30 nm thick, the light-emitting layer 110 was 25 nm thick, the electron transport layer 112 was 25 nm thick, the electron injection layer 114 was 1 nm thick, and the cathode 116 was 100 nm thick.

While power was connected to the anode 104 and the cathode 116 to allow current to flow through the organic EL device 100 in which compound 3, compound 16, compound 4 or comparative compound 1 was used as a host material of the light-emitting layer, the current efficiency and half-life of the organic EL device 100 were measured. The measured results are shown in Table 1, below. The current efficiency was measured at 10 mA/cm$^2$, and the half-life was measured at 1000 cd/m$^2$.

TABLE 1

|  | Compound 3 | Compound 16 | Compound 4 | Comparative compound 1 |
|---|---|---|---|---|
| Voltage (V) | 4.0 | 4.4 | 4.9 | 5.5 |
| Luminous efficiency (cd/A) | 36.1 | 33.3 | 30.1 | 28.7 |
| Half-life (hr) | 2800 | 1750 | 1300 | 1100 |

As may be seen in Table 1, compared to the organic EL device that used Comparative compound 1 as a host material of the light-emitting layer, the organic EL devices that used an azacarbazole derivative having a carbazole group according to an embodiment as a host material (that is, one of compound 3, compound 16 or compound 4) showed improved luminous efficiency and an improved half-life. Particularly, it is seen that the organic EL device that used compound 3, having a structure in which a phenyl group is attached to a carbon (C) atom adjacent to a nitrogen (N) atom of an azacarbazole ring, as a host material showed a remarkably improved half-life.

An organic EL device according to embodiments and including the azacarbazole derivative having the carbazole group may have any suitable configuration. As shown above, the azacarbazole derivative having a carbazole group according to embodiments may be used as an organic EL material of a passive type organic EL device. In other implementations, the azacarbazole derivative having the carbazole group may be also used as an organic EL material of an active type organic EL device to thus improve the luminous efficiency of the active type organic EL device and realize long life. It is to be understood that more than or fewer than the layers shown in FIG. 1 may be included in an organic EL device the azacarbazole derivative having a carbazole group according to embodiments.

As described above, by using the azacarbazole derivative having a carbazole group according to embodiments as a host material of an organic EL material, particularly as a host material of a phosphorescent light-emitting layer, the luminous efficiency of the organic EL device in a green light-emitting region may be improved and a long life may be realized. Also, the azacarbazole derivative having a carbazole derivative according to embodiments may be changed in various forms.

The organic EL device which uses the azacarbazole derivative having the carbazole group according to embodiments as a host material of a light-emitting layer may be employed in an organic EL display, a lighting apparatus, etc.

By way of summation and review, in an application of the organic EL device to a display apparatus, high efficiency and long life of the organic EL device are desirable, and for realizing the high efficiency and long life, normalization, stabilization and durability of the hole transport layer are considered.

Various compounds such as an aromatic amine-based compound and the like that may be used for each layer of an organic EL device may be used. For example, an azacarbazole derivative has been proposed as a host material of a light-emitting layer, as a hole transport material, as a material for a cathode buffer layer, or as a material for a hole stop layer. Also, a carbazole derivative has been proposed, for example, as a host material, an electron transport material, or a material for a barrier layer for preventing excitons generated in a light-emitting layer from being diffused into an electron transport region. However, organic EL devices employing these materials have fail to exhibit sufficient luminous efficiency. Accordingly, an organic EL device that may be driven at a low voltage with higher efficiency and has long luminous lifespan is desirable.

Embodiments provide organic EL materials in which luminous efficiency is improved and a long life is realized.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescence material represented by Formula 1, below:

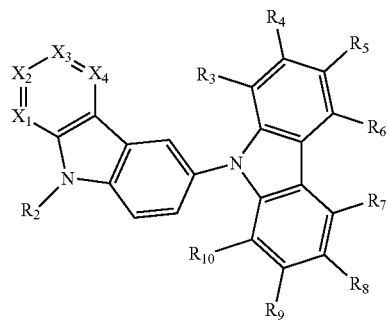

Formula 1 wherein:

$X_1$, $X_2$, $X_3$ and $X_4$ are each independently a nitrogen atom or a carbon atom that is monovalently bonded to a substituent $R_1$, where $R_1$ is a hydrogen atom, a halogen atom, an aryl group having 6 to 18 carbon atoms, a heteroaryl group having 6 to 18 carbon atoms, an alkyl group having 1 to 12 carbon atoms or a cycloalkyl group having 3 to 12 carbon atoms;

$R_2$, $R_3$, $R_4$, $R_5$, $R_6$, $R_7$, $R_8$, $R_9$ and $R_{10}$ are each independently an aryl group having 6 to 30 carbon atoms or a heteroaryl group having 6 to 30 carbon atoms; and at least one of $X_1$, $X_2$, $X_3$ and $X_4$ is a nitrogen atom.

2. The organic electroluminescence material as claimed in claim 1, wherein one or more of $R_2$, $R_3$, $R_4$, $R_5$, $R_6$, $R_7$, $R_8$, $R_9$ and $R_{10}$ are independently one of the monovalent groups represented by Group (2), Group (3), Group (4), Group (5), Group (6), Group (7), Group (8), Group (9), Group (10), or Group (11), below:

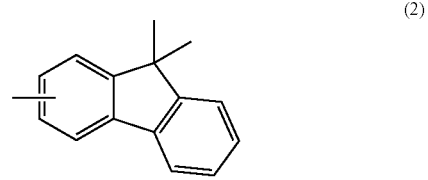

(2)

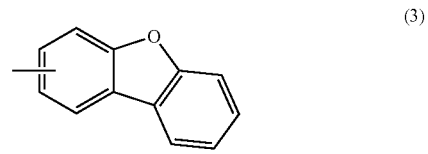

(3)

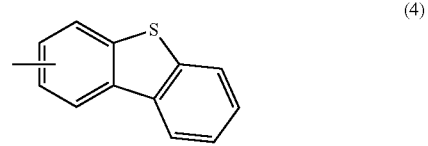

(4)

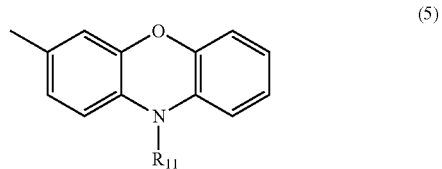

(5)

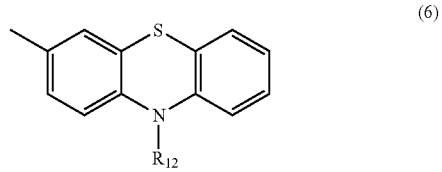

(6)

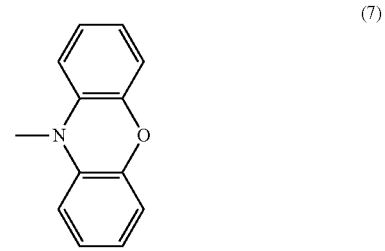

(7)

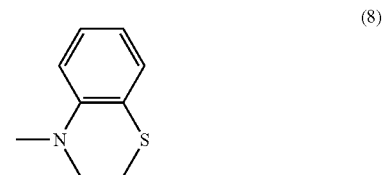

(8)

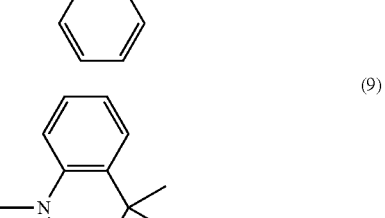

(9)

-continued

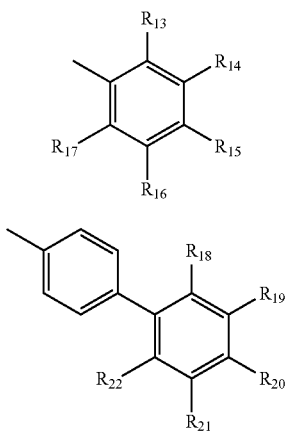
(10)

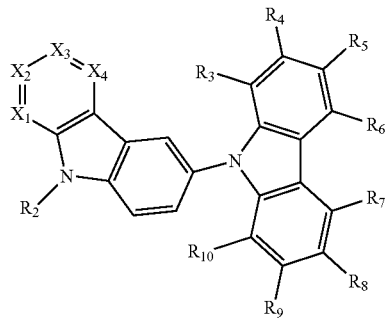
(11)

where $R_{11}, R_{12}, R_{13}, R_{14}, R_{15}, R_{16}, R_{17}, R_{18}, R_{19}, R_{20}, R_{21}$, and $R_{22}$ are each independently a hydrogen atom, a halogen atom, an aryl group having 6 to 18 carbon atoms, a heteroaryl group having 6 to 18 carbon atoms, or an alkyl group having 1 to 12 carbon atoms.

3. The organic electroluminescence material as claimed in claim 1 wherein $R_1$ is a phenyl group, a methyl group, or a cyclohexyl group.

4. An organic electroluminescence device comprising an organic electroluminescence material represented by Formula 1, below:

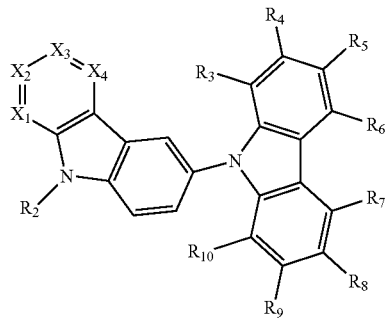

Formula 1 wherein:

$X_1, X_2, X_3$ and $X_4$ are each independently a nitrogen atom or a carbon atom that is monovalently bonded to a substituent $R_1$, where $R_1$ is a hydrogen atom, a halogen atom, an aryl group having 6 to 18 carbon atoms, a heteroaryl group having 6 to 18 carbon atoms, an alkyl group having 1 to 12 carbon atoms or a cycloalkyl group having 3 to 12 carbon atoms;

$R_2, R_3, R_4, R_5, R_6, R_7, R_8, R_9$ and $R_{10}$ are each independently an aryl group having 6 to 30 carbon atoms or a heteroaryl group having 6 to 30 carbon atoms; and at least one of $X_1, X_2, X_3$ and $X_4$ is a nitrogen atom.

5. The organic electroluminescence device as claimed in claim 4, wherein one or more of $R_2, R_3, R_4, R_5, R_6, R_7, R_8, R_9$, and $R_{10}$ are independently one of the monovalent groups represented by Group (2), Group (3), Group (4), Group (5), Group (6), Group (7), Group (8), Group (9), Group (10), or Group (11), below:

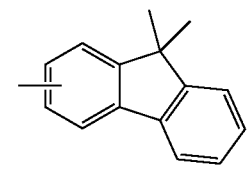
(2)

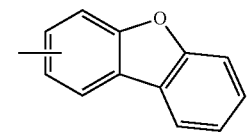
(3)

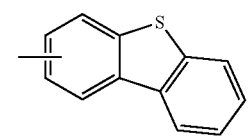
(4)

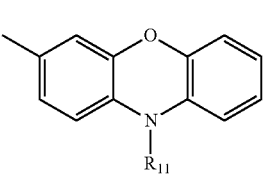
(5)

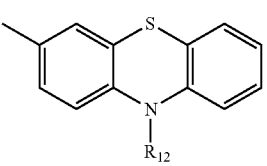
(6)

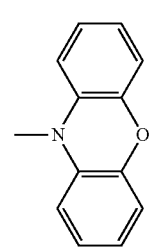
(7)

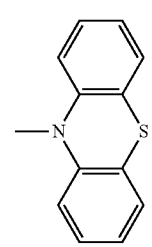
(8)

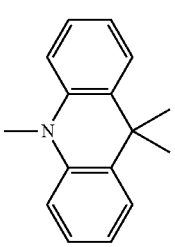
(9)

49
-continued

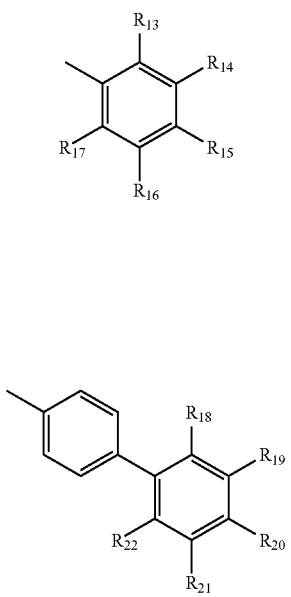

(10)

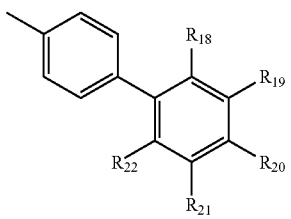

(11)

where $R_{11}, R_{12}, R_{13}, R_{14}, R_{15}, R_{16}, R_{17}, R_{18}, R_{19}, R_{20}, R_{21}$, and $R_{22}$ are each independently a hydrogen atom, a halogen atom, an aryl group having 6 to 18 carbon atoms or heteroaryl group having 6 to 18 carbon atoms, or an alkyl group having 1 to 12 carbon atoms.

6. The organic electroluminescence device as claimed in claim 4, wherein $R_1$ is a phenyl group, a methyl group, or a cyclohexyl group.

7. An organic electroluminescence device comprising an organic electroluminescence material represented by any one of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45 and 46, below:

1

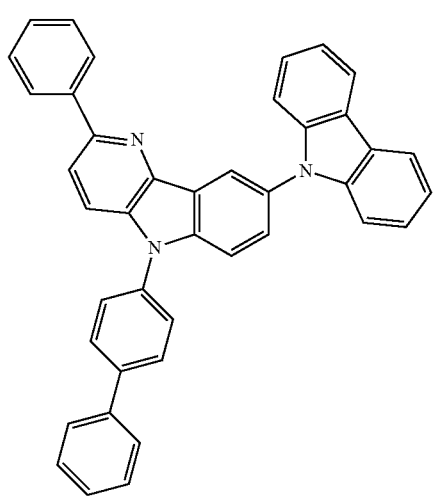

50
-continued

2

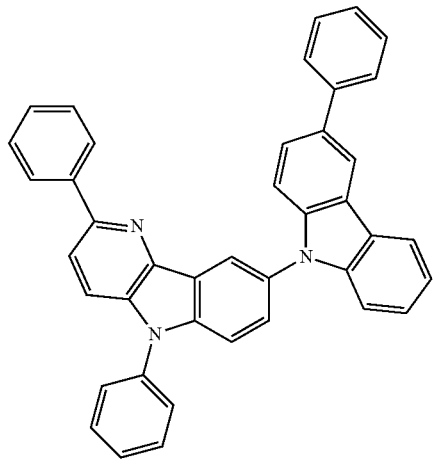

3

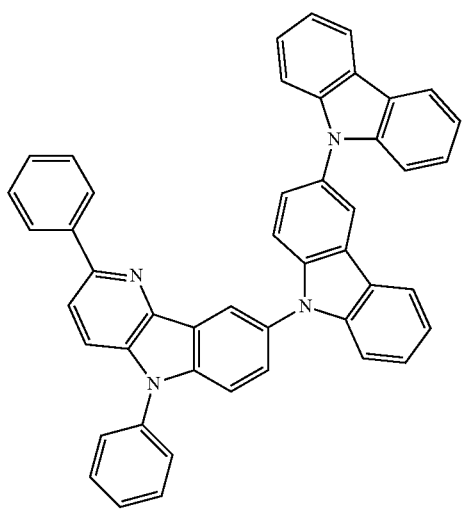

4

5
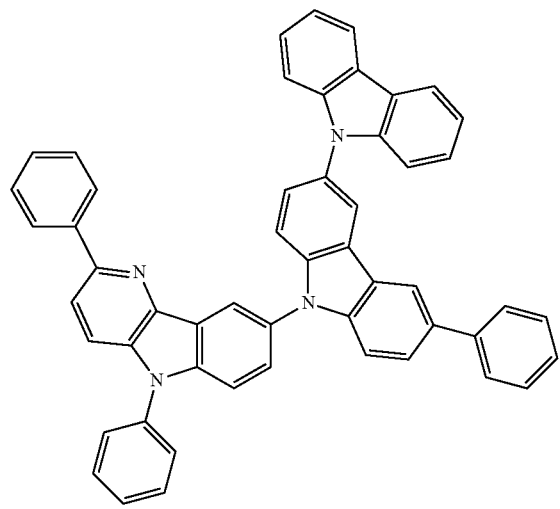
6
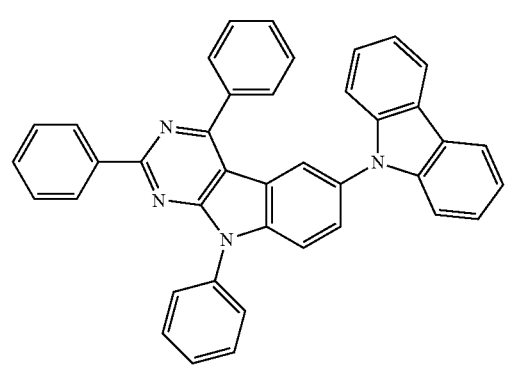
7
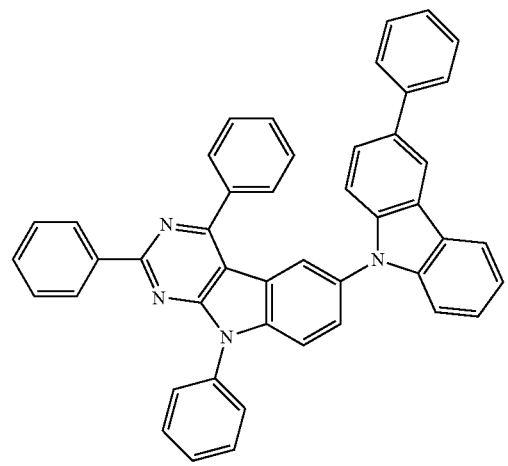
8
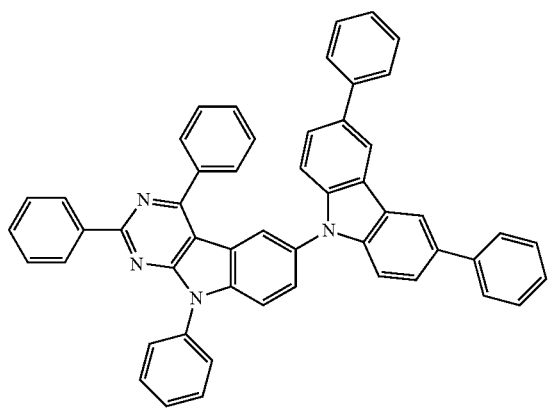
9
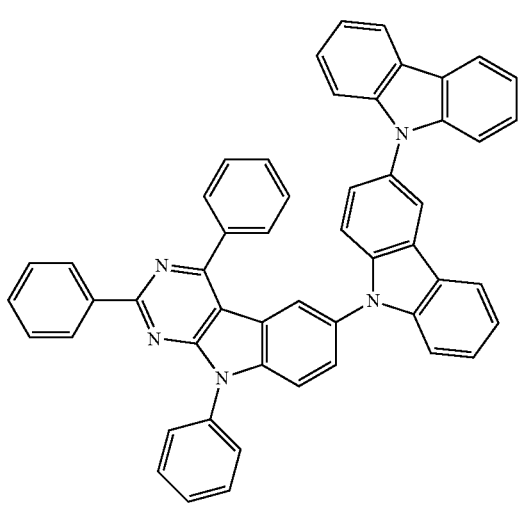
10
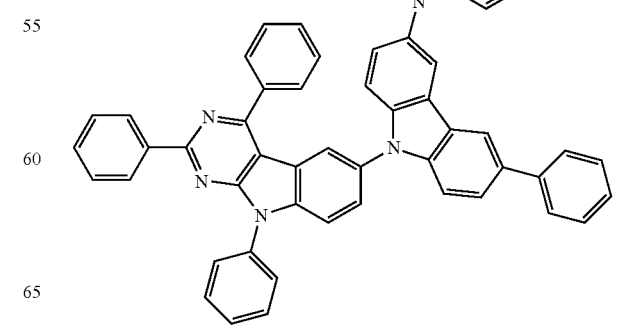

11
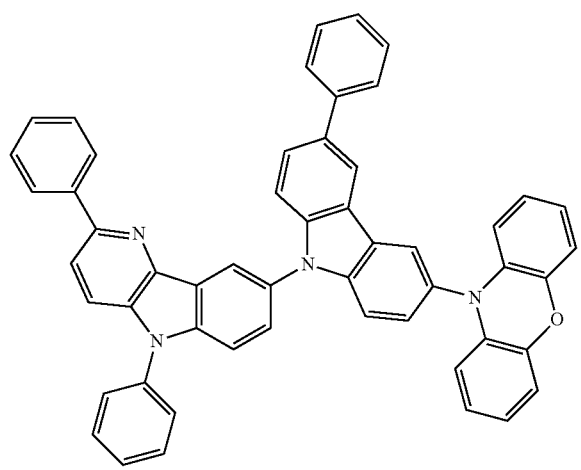
12
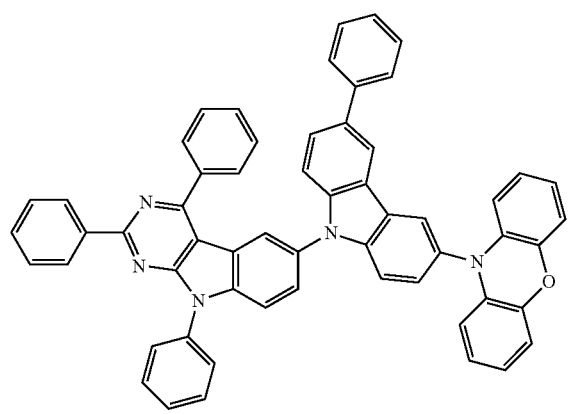
13
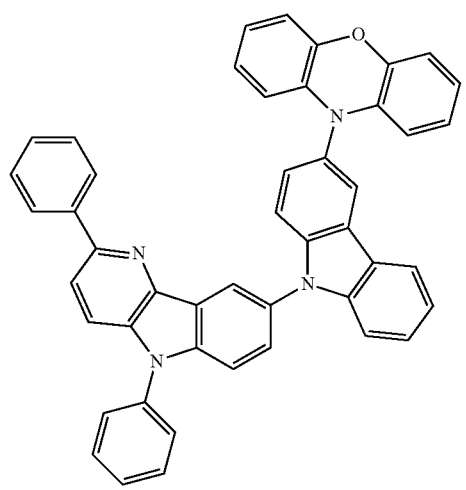
14
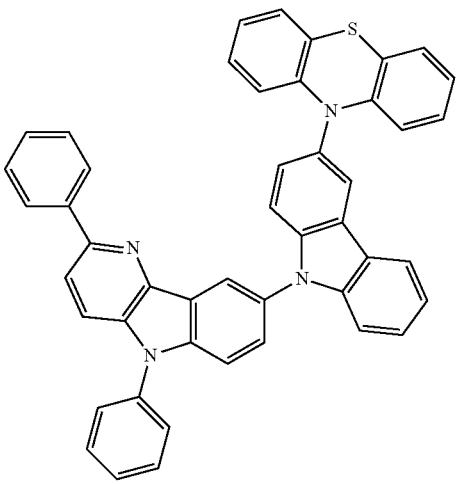
15
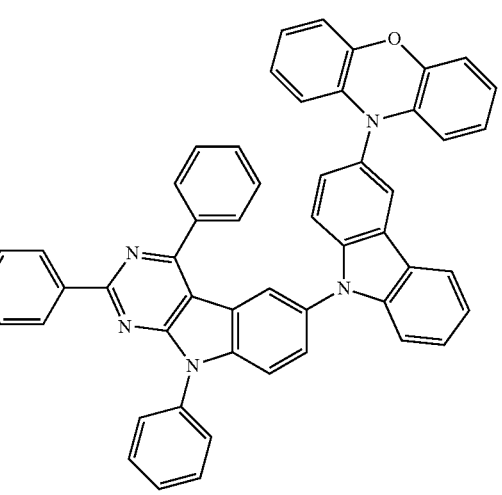
16
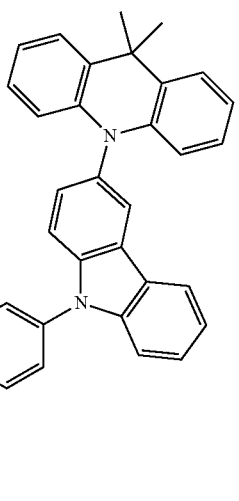

17
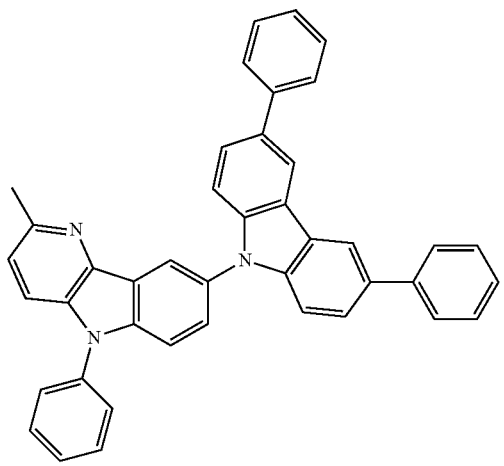
18
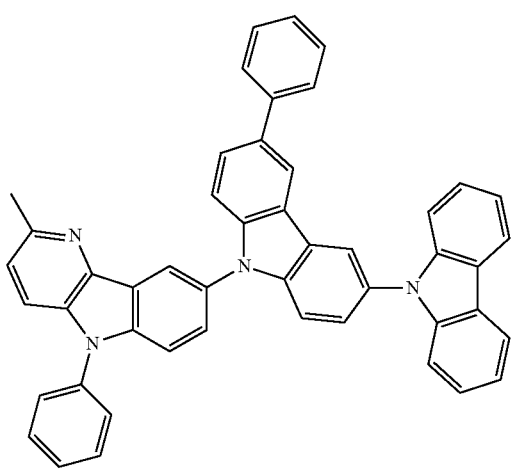
19
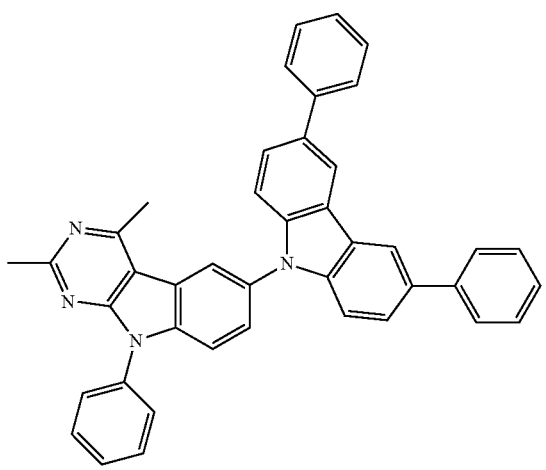
20
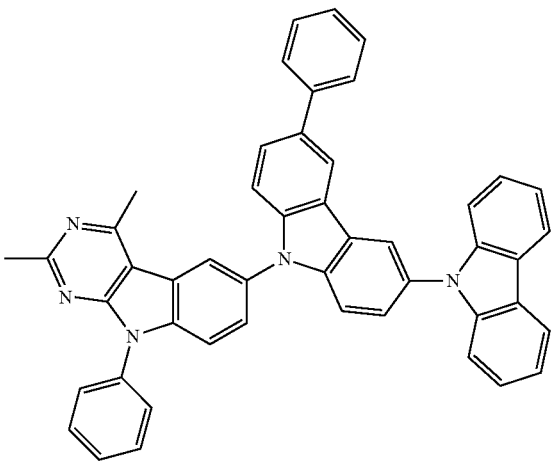
21
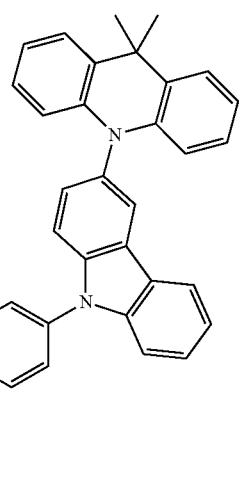
22
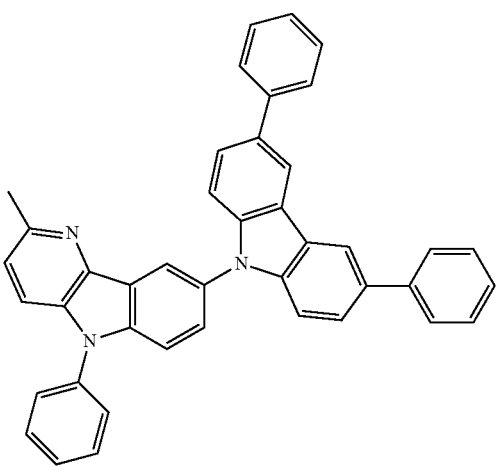

23
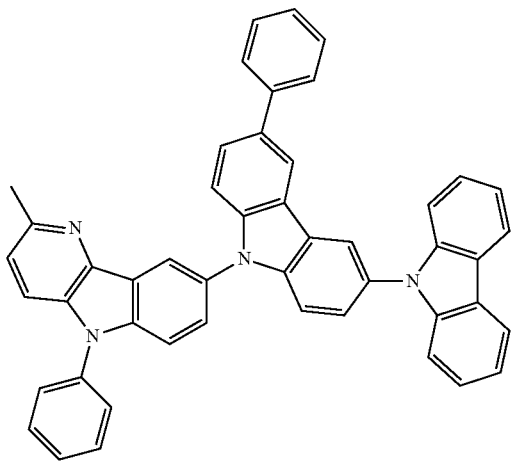
26
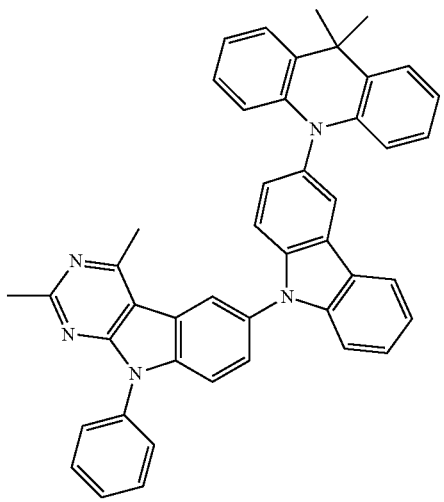
24
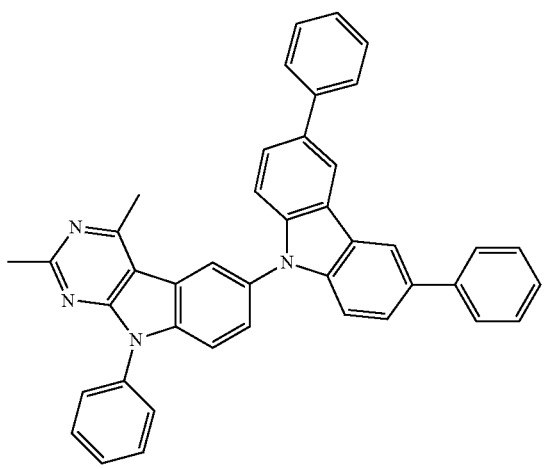
27
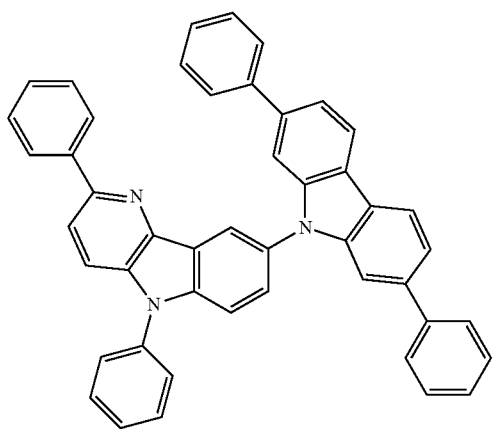
25
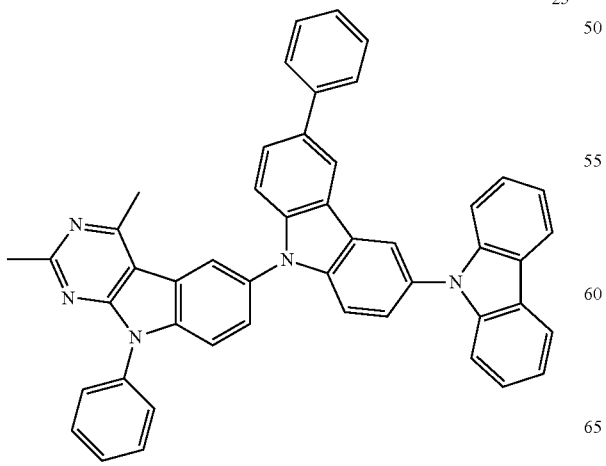
28
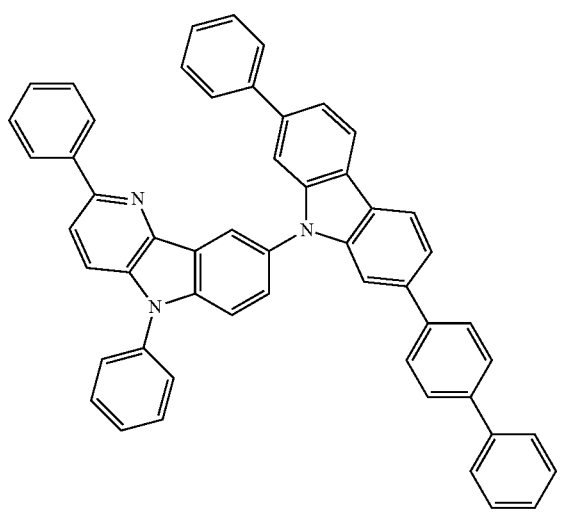

29
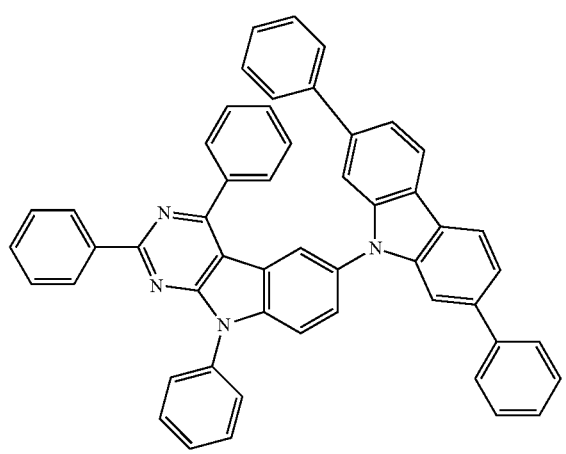
30
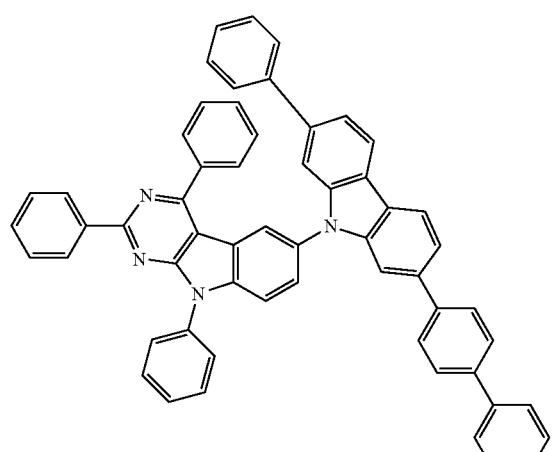
31
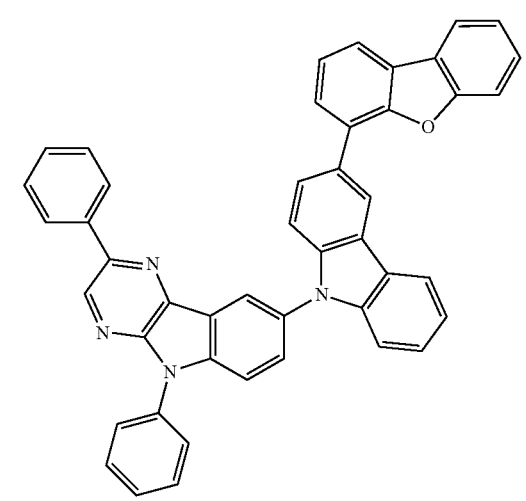
32
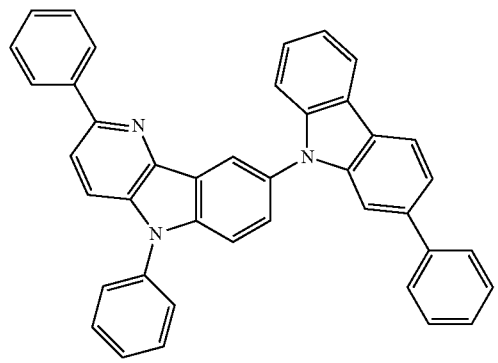
33
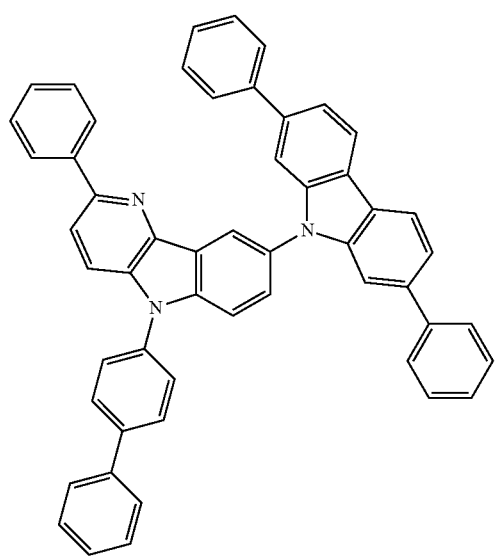
34
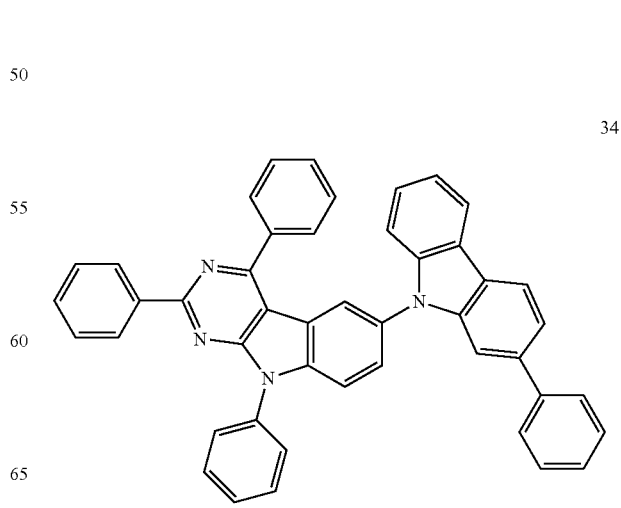

35
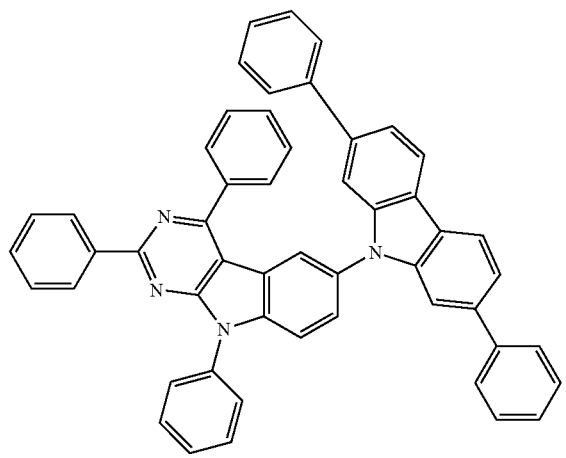
36
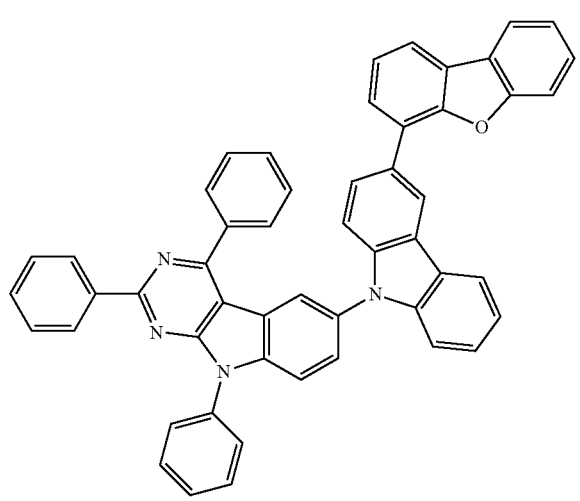
37
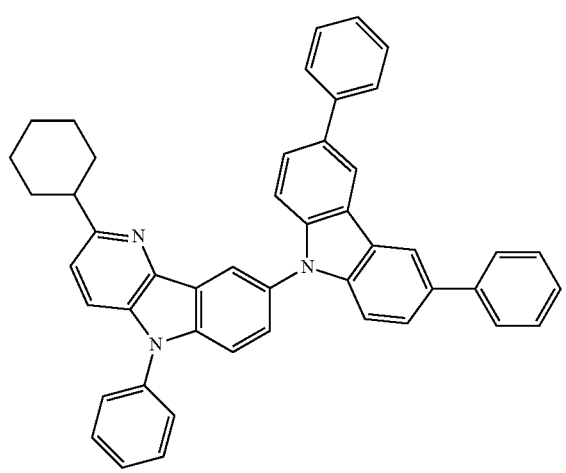
38
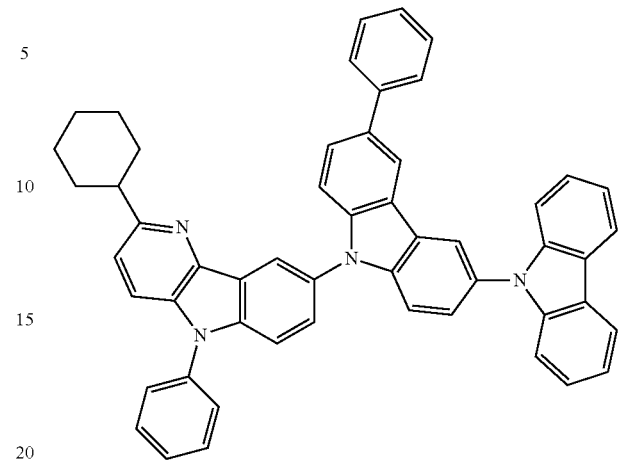
39
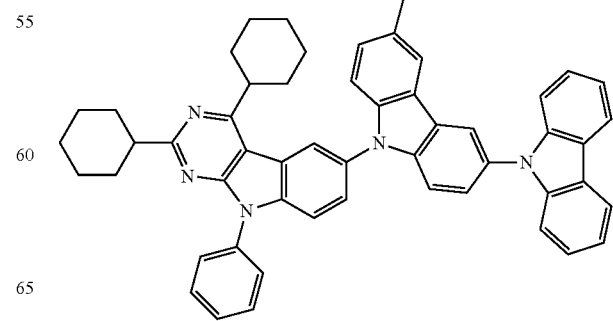
40

41
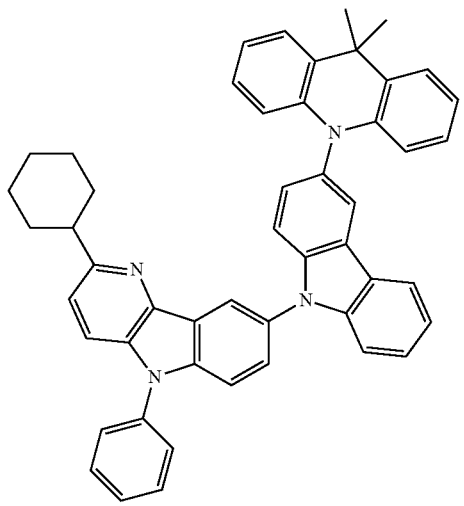
42
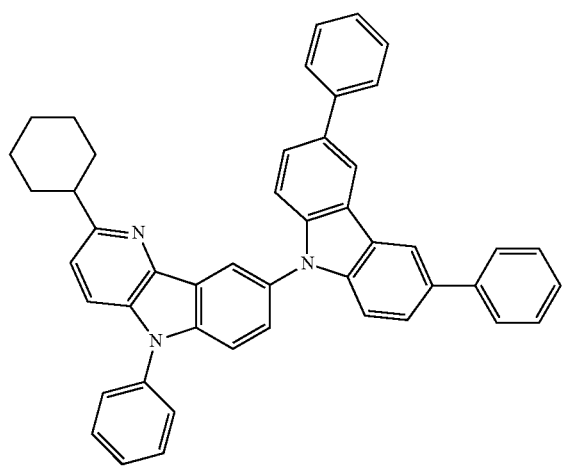
43
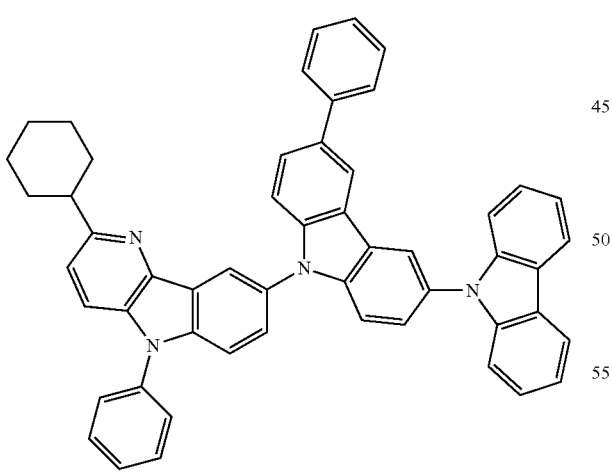
44
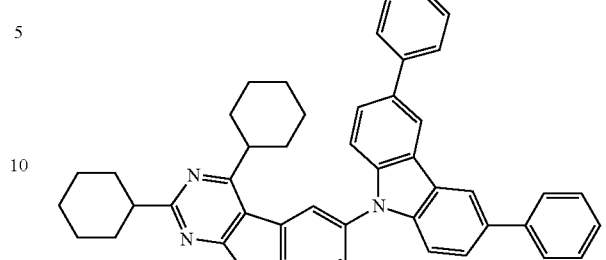
45
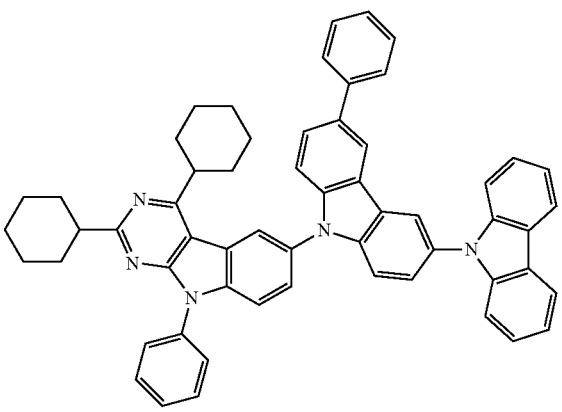
46
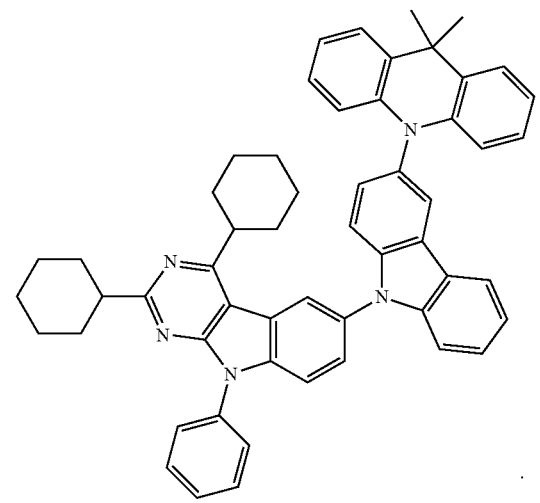
* * * * *